United States Patent
Murphy et al.

(10) Patent No.: US 11,278,282 B2
(45) Date of Patent: Mar. 22, 2022

(54) STAPLING DEVICE WITH SELECTIVE CUTTING

(71) Applicant: Covidien LP, Mansfield, MA (US)

(72) Inventors: Quintin D. Murphy, Covington, GA (US); Sachin P. Budhabhatti, Unionville, CT (US)

(73) Assignee: Covidien LP, Mansfield, MA (US)

( * ) Notice: Subject to any disclaimer, the term of this patent is extended or adjusted under 35 U.S.C. 154(b) by 110 days.

(21) Appl. No.: 16/778,007

(22) Filed: Jan. 31, 2020

(65) Prior Publication Data

US 2021/0236122 A1  Aug. 5, 2021

(51) Int. Cl.
*A61B 17/072* (2006.01)

(52) U.S. Cl.
CPC ...... *A61B 17/072* (2013.01); *A61B 17/07207* (2013.01); *A61B 2017/07257* (2013.01); *A61B 2017/07271* (2013.01); *A61B 2017/07278* (2013.01); *A61B 2017/07285* (2013.01)

(58) Field of Classification Search
CPC ........ A61B 17/072; A61B 2017/07257; A61B 2017/07271; A61B 2017/07285
USPC ...................................... 227/180.1
See application file for complete search history.

(56) References Cited

U.S. PATENT DOCUMENTS

| | | |
|---|---|---|
| 3,499,591 A | 3/1970 | Green |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,241,861 A | 12/1980 | Fleischer |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |

(Continued)

FOREIGN PATENT DOCUMENTS

| | | |
|---|---|---|
| AU | 198654765 | 9/1986 |
| CA | 2773414 A1 | 11/2012 |

(Continued)

OTHER PUBLICATIONS

Extended European Search Report dated Jun. 28, 2021, issued in corresponding EP Appln. No. 21154211, 12 pages.

(Continued)

*Primary Examiner* — Valentin Neacsu

(57) ABSTRACT

A surgical stapling device includes a drive assembly and a knife bar assembly that can be selectively coupled together or uncoupled from each other to place the stapling device in a cutting mode or in a non-cutting mode. The stapling device may also include a locking member that locks a distal portion of the anvil to a distal portion of the cartridge assembly to define a maximum tissue gap between the anvil and the cartridge assembly.

16 Claims, 15 Drawing Sheets

(56) References Cited

U.S. PATENT DOCUMENTS

| | | |
|---|---|---|
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |

(56) References Cited

U.S. PATENT DOCUMENTS

| | | |
|---|---|---|
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Billner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,690,675 A | 11/1997 | Sawyer et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson, IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |

(56) References Cited

U.S. PATENT DOCUMENTS

| | | |
|---|---|---|
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,267,682 B1 | 9/2007 | Bender et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |

(56) References Cited

U.S. PATENT DOCUMENTS

| | | |
|---|---|---|
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,896 B2 | 10/2010 | Racenet |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,630 B2 | 11/2010 | Damadian et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |

(56) References Cited

U.S. PATENT DOCUMENTS

| | | |
|---|---|---|
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,193,044 B2 | 6/2012 | Kenneth |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,215,532 B2 | 7/2012 | Marczyk |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,245,931 B2 | 8/2012 | Shigeta |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,300 B2 | 9/2012 | Boudreaux |
| 8,272,551 B2 | 9/2012 | Knodel et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |
| 8,286,850 B2 | 10/2012 | Viola |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,044 B2 | 11/2012 | Viola |
| 8,308,046 B2 | 11/2012 | Prommersberger |
| 8,308,757 B2 | 11/2012 | Hillstead et al. |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |

(56) References Cited

U.S. PATENT DOCUMENTS

| | | |
|---|---|---|
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czernik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,240 B1 | 8/2013 | Mata et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,461 B2 | 11/2013 | Shelton, IV et al. |
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,762 B2 | 11/2013 | Hess et al. |
| 8,596,515 B2 | 12/2013 | Okoniewski |
| 8,602,288 B2 | 12/2013 | Shelton, IV et al. |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,430 B2 | 12/2013 | (Prommersberger) Stopek et al. |
| 8,627,994 B2 | 1/2014 | Zemlok et al. |
| 8,628,544 B2 | 1/2014 | Farascioni |
| 8,631,988 B2 | 1/2014 | Viola |
| 8,631,989 B2 | 1/2014 | Aranyi et al. |
| 8,631,991 B2 | 1/2014 | Cropper et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |

(56) References Cited

U.S. PATENT DOCUMENTS

| | | |
|---|---|---|
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 | 3/2014 | Wazer et al. |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,684,253 B2 | 4/2014 | Giordano et al. |
| 8,690,039 B2 | 4/2014 | Beardsley et al. |
| 8,695,865 B2 | 4/2014 | Smith et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,701,961 B2 | 4/2014 | Ivanko |
| 8,708,213 B2 | 4/2014 | Shelton, IV et al. |
| 8,714,429 B2 | 5/2014 | Demmy |
| 8,715,277 B2 | 5/2014 | Weizman |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,752,748 B2 | 6/2014 | Whitman et al. |
| 8,752,749 B2 | 6/2014 | Moore et al. |
| 8,757,465 B2 | 6/2014 | Woodard, Jr. et al. |
| 8,758,391 B2 | 6/2014 | Swayze et al. |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,607 B2 | 9/2014 | Marczyk |
| 8,827,133 B2 | 9/2014 | Shelton, IV et al. |
| 8,827,134 B2 | 9/2014 | Viola et al. |
| 8,833,631 B2 | 9/2014 | Munro, III et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,788 B2 | 9/2014 | Knodel |
| 8,851,354 B2 | 10/2014 | Swensgard et al. |
| 8,851,355 B2 | 10/2014 | Aranyi et al. |
| 8,857,693 B2 | 10/2014 | Schuckmann et al. |
| 8,864,007 B2 | 10/2014 | Widenhouse et al. |
| 8,864,009 B2 | 10/2014 | Shelton, IV et al. |
| 8,875,971 B2 | 11/2014 | Hall et al. |
| 8,875,972 B2 | 11/2014 | Weisenburgh, II et al. |
| 8,893,949 B2 | 11/2014 | Shelton, IV et al. |
| 8,893,950 B2 | 11/2014 | Marczyk |
| 8,899,461 B2 | 12/2014 | Farascioni |
| 8,899,463 B2 | 12/2014 | Schall et al. |
| 8,899,464 B2 | 12/2014 | Hueil et al. |
| 8,900,616 B2 | 12/2014 | Belcheva et al. |
| 8,920,435 B2 | 12/2014 | Smith et al. |
| 8,925,782 B2 | 1/2015 | Shelton, IV |
| 8,926,598 B2 | 1/2015 | Mollere et al. |
| 8,931,682 B2 | 1/2015 | Timm et al. |
| 8,931,693 B1 | 1/2015 | Kumar et al. |
| 8,955,732 B2 | 2/2015 | Zemlok et al. |
| 8,958,429 B2 | 2/2015 | Shukla et al. |
| 8,960,517 B2 | 2/2015 | Lee |
| 8,967,443 B2 | 3/2015 | McCuen |
| 8,967,446 B2 | 3/2015 | Beardsley et al. |
| 8,973,803 B2 | 3/2015 | Hall et al. |
| 8,978,954 B2 | 3/2015 | Shelton, IV et al. |
| 8,978,956 B2 | 3/2015 | Schall et al. |
| 8,998,060 B2 | 4/2015 | Bruewer et al. |
| 9,005,230 B2 | 4/2015 | Yates et al. |
| 9,010,607 B2 | 4/2015 | Kostrzewski |
| 9,016,539 B2 | 4/2015 | Kostrzewski et al. |
| 9,016,541 B2 | 4/2015 | Viola et al. |
| 9,016,542 B2 | 4/2015 | Shelton, IV et al. |
| 9,016,546 B2 | 4/2015 | Demmy et al. |
| 9,022,271 B2 | 5/2015 | Scirica |
| 9,027,817 B2 | 5/2015 | Milliman et al. |
| 9,033,203 B2 | 5/2015 | Woodard, Jr. et al. |
| 9,044,228 B2 | 6/2015 | Woodard, Jr. et al. |
| 9,044,229 B2 | 6/2015 | Scheib et al. |
| 9,050,084 B2 | 6/2015 | Schmid et al. |
| 9,055,941 B2 | 6/2015 | Schmid et al. |
| 9,060,770 B2 | 6/2015 | Shelton, IV et al. |
| 9,072,535 B2 | 7/2015 | Shelton, IV et al. |
| 9,089,326 B2 | 7/2015 | Krumanaker et al. |
| 9,101,359 B2 | 8/2015 | Smith et al. |
| 9,107,663 B2 | 8/2015 | Swensgard |
| 9,107,664 B2 | 8/2015 | Marczyk |
| 9,113,862 B2 | 8/2015 | Morgan et al. |
| 9,113,864 B2 | 8/2015 | Morgan et al. |
| 9,113,870 B2 | 8/2015 | Viola |
| 9,113,872 B2 | 8/2015 | Viola |
| 9,113,880 B2 | 8/2015 | Zemlok et al. |
| 9,125,649 B2 | 9/2015 | Bruewer et al. |
| 9,138,225 B2 | 9/2015 | Huang et al. |
| 9,155,537 B2 | 10/2015 | Katre et al. |
| 9,179,912 B2 | 11/2015 | Yates et al. |
| 9,192,378 B2 | 11/2015 | Aranyi et al. |
| 9,192,379 B2 | 11/2015 | Aranyi et al. |
| 9,192,384 B2 | 11/2015 | Bettuchi |
| 9,198,644 B2 | 12/2015 | Balek et al. |
| 9,198,661 B2 | 12/2015 | Swensgard |
| 9,204,876 B2 | 12/2015 | Cappola et al. |
| 9,216,019 B2 | 12/2015 | Schmid et al. |
| 9,216,020 B2 | 12/2015 | Zhang et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,232,941 B2 | 1/2016 | Mandakolathur Vasudevan et al. |
| 9,232,944 B2 | 1/2016 | Cappola et al. |
| 9,237,891 B2 | 1/2016 | Shelton, IV |
| 9,254,180 B2 | 2/2016 | Huitema et al. |
| 9,265,585 B2 | 2/2016 | Wingardner et al. |
| 9,271,728 B2 | 3/2016 | Gupta et al. |
| 9,277,919 B2 | 3/2016 | Timmer et al. |
| 9,282,962 B2 | 3/2016 | Schmid et al. |
| 9,283,054 B2 | 3/2016 | Morgan et al. |
| 9,289,209 B2 | 3/2016 | Gurumurthy et al. |
| 9,289,210 B2 | 3/2016 | Baxter, III et al. |
| 9,289,225 B2 | 3/2016 | Shelton, IV et al. |
| 9,295,464 B2 | 3/2016 | Shelton, IV et al. |
| 9,295,465 B2 | 3/2016 | Farascioni |
| 9,301,752 B2 | 4/2016 | Mandakolathur Vasudevan et al. |
| 9,301,753 B2 | 4/2016 | Aldridge et al. |
| 9,301,757 B2 | 4/2016 | Williams |
| 9,307,965 B2 | 4/2016 | Ming et al. |
| 9,307,986 B2 | 4/2016 | Hall et al. |
| 9,307,989 B2 | 4/2016 | Shelton, IV et al. |
| 9,314,246 B2 | 4/2016 | Shelton, IV et al. |
| 9,320,518 B2 | 4/2016 | Henderson et al. |
| 9,320,521 B2 | 4/2016 | Shelton, IV et al. |
| 9,326,767 B2 | 5/2016 | Koch, Jr. et al. |
| 9,332,987 B2 | 5/2016 | Leimbach et al. |
| 9,345,477 B2 | 5/2016 | Anim et al. |

(56) References Cited

U.S. PATENT DOCUMENTS

| | | |
|---|---|---|
| 9,345,478 B2 | 5/2016 | Knodel |
| 9,345,481 B2 | 5/2016 | Hall et al. |
| 9,345,780 B2 | 5/2016 | Manoharan et al. |
| 9,351,727 B2 | 5/2016 | Leimbach et al. |
| 9,351,732 B2 | 5/2016 | Hodgkinson |
| 9,358,003 B2 | 6/2016 | Hall et al. |
| 9,364,217 B2 | 6/2016 | Kostrzewski et al. |
| 9,364,218 B2 | 6/2016 | Scirica |
| 9,364,219 B2 | 6/2016 | Olson et al. |
| 9,364,220 B2 | 6/2016 | Williams |
| 9,364,233 B2 | 6/2016 | Alexander, III et al. |
| 9,370,358 B2 | 6/2016 | Shelton, IV et al. |
| 9,370,362 B2 | 6/2016 | Petty et al. |
| 9,386,983 B2 | 7/2016 | Swensgard et al. |
| 9,386,984 B2 | 7/2016 | Aronhalt et al. |
| 9,386,988 B2 | 7/2016 | Baxter, III et al. |
| 9,393,018 B2 | 7/2016 | Wang et al. |
| 9,398,911 B2 | 7/2016 | Auld |
| 9,402,604 B2 | 8/2016 | Williams et al. |
| 9,421,014 B2 | 8/2016 | Ingmanson et al. |
| 9,433,419 B2 | 9/2016 | Gonzalez et al. |
| 9,433,420 B2 | 9/2016 | Hodgkinson |
| 9,445,810 B2 | 9/2016 | Cappola |
| 9,445,813 B2 | 9/2016 | Shelton, IV et al. |
| 9,451,959 B2 | 9/2016 | Patankar et al. |
| 9,468,438 B2 | 10/2016 | Baber et al. |
| 9,468,439 B2 | 10/2016 | Cappola et al. |
| 9,480,476 B2 | 11/2016 | Aldridge et al. |
| 9,480,492 B2 | 11/2016 | Aranyi et al. |
| 9,492,171 B2 | 11/2016 | Patenaude |
| 9,498,212 B2 | 11/2016 | Racenet et al. |
| 9,510,827 B2 | 12/2016 | Kostrzewski |
| 9,517,065 B2 | 12/2016 | Simms et al. |
| 9,517,066 B2 | 12/2016 | Racenet et al. |
| 9,539,007 B2 | 1/2017 | Dhakad et al. |
| 9,549,735 B2 | 1/2017 | Shelton, IV et al. |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0006429 A1 | 1/2005 | Wales et al. |
| 2005/0216055 A1 | 9/2005 | Scirica et al. |
| 2006/0049229 A1 | 3/2006 | Milliman et al. |
| 2006/0180634 A1 | 8/2006 | Shelton et al. |
| 2006/0289602 A1 | 12/2006 | Wales et al. |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179528 A1 | 8/2007 | Soltz et al. |
| 2007/0194079 A1 | 8/2007 | Hueil et al. |
| 2007/0194082 A1 | 8/2007 | Morgan et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0110961 A1 | 5/2008 | Voegele et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0090763 A1 | 4/2009 | Zemlok et al. |
| 2009/0090766 A1 | 4/2009 | Knodel |
| 2009/0242610 A1 | 10/2009 | Shelton, IV et al. |
| 2009/0255974 A1 | 10/2009 | Viola |
| 2009/0308907 A1 | 12/2009 | Nalagatla et al. |
| 2010/0012703 A1 | 1/2010 | Calabrese et al. |
| 2010/0069942 A1 | 3/2010 | Shelton, IV |
| 2010/0127041 A1 | 5/2010 | Morgan et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0193566 A1 | 8/2010 | Scheib et al. |
| 2010/0224668 A1 | 9/2010 | Fontayne et al. |
| 2010/0249802 A1 | 9/2010 | May et al. |
| 2010/0252611 A1 | 10/2010 | Ezzat et al. |
| 2010/0282820 A1* | 11/2010 | Kasvikis ............... A61B 17/068 227/181.1 |
| 2011/0006101 A1 | 1/2011 | Hall et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0087276 A1 | 4/2011 | Bedi et al. |
| 2011/0101069 A1 | 5/2011 | Bombard et al. |
| 2011/0114702 A1 | 5/2011 | Farascioni |
| 2011/0121049 A1 | 5/2011 | Malinouskas et al. |
| 2011/0147433 A1 | 6/2011 | Shelton, IV et al. |
| 2011/0155787 A1 | 6/2011 | Baxter, III et al. |
| 2011/0163146 A1 | 7/2011 | Ortiz et al. |
| 2011/0163149 A1 | 7/2011 | Viola |
| 2011/0186614 A1* | 8/2011 | Kasvikis ............... A61B 17/068 227/175.2 |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0204119 A1 | 8/2011 | McCuen |
| 2011/0278343 A1 | 11/2011 | Knodel et al. |
| 2011/0290856 A1 | 12/2011 | Shelton, IV et al. |
| 2012/0016362 A1 | 1/2012 | Heinrich et al. |
| 2012/0053406 A1 | 3/2012 | Conlon et al. |
| 2012/0061446 A1 | 3/2012 | Knodel et al. |
| 2012/0074200 A1 | 3/2012 | Schmid et al. |
| 2012/0080478 A1 | 4/2012 | Morgan et al. |
| 2012/0080495 A1 | 4/2012 | Holcomb et al. |
| 2012/0080498 A1 | 4/2012 | Shelton, IV et al. |
| 2012/0091183 A1 | 4/2012 | Manoux et al. |
| 2012/0138659 A1 | 6/2012 | Marczyk et al. |
| 2012/0175399 A1 | 7/2012 | Shelton et al. |
| 2012/0181322 A1 | 7/2012 | Whitman et al. |
| 2012/0187179 A1 | 7/2012 | Gleiman |
| 2012/0193394 A1 | 8/2012 | Holcomb et al. |
| 2012/0193399 A1 | 8/2012 | Holcomb et al. |
| 2012/0199632 A1 | 8/2012 | Spivey et al. |
| 2012/0211542 A1 | 8/2012 | Racenet |
| 2012/0223121 A1 | 9/2012 | Viola et al. |
| 2012/0234895 A1 | 9/2012 | O'Connor et al. |
| 2012/0234897 A1 | 9/2012 | Shelton, IV et al. |
| 2012/0241492 A1 | 9/2012 | Shelton, IV et al. |
| 2012/0241493 A1 | 9/2012 | Baxter, III et al. |
| 2012/0241504 A1 | 9/2012 | Soltz et al. |
| 2012/0248169 A1 | 10/2012 | Widenhouse et al. |
| 2012/0286021 A1 | 11/2012 | Kostrzewski |
| 2012/0286022 A1 | 11/2012 | Olson et al. |
| 2012/0298722 A1 | 11/2012 | Hess et al. |
| 2013/0008937 A1 | 1/2013 | Viola |
| 2013/0012983 A1 | 1/2013 | Kleyman |
| 2013/0015231 A1 | 1/2013 | Kostrzewski |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037595 A1 | 2/2013 | Gupta et al. |
| 2013/0041406 A1 | 2/2013 | Bear et al. |
| 2013/0068815 A1 | 3/2013 | Bruewer et al. |
| 2013/0068816 A1 | 3/2013 | Mandakolathur Vasudevan et al. |
| 2013/0068818 A1 | 3/2013 | Kasvikis |
| 2013/0075447 A1 | 3/2013 | Weisenburgh, II et al. |
| 2013/0092717 A1 | 4/2013 | Marczyk et al. |
| 2013/0098964 A1 | 4/2013 | Smith et al. |

(56) References Cited

U.S. PATENT DOCUMENTS

| | | |
|---|---|---|
| 2013/0098966 A1 | 4/2013 | Kostrzewski et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105552 A1 | 5/2013 | Weir et al. |
| 2013/0105553 A1 | 5/2013 | (Tarinelli) Racenet et al. |
| 2013/0112730 A1 | 5/2013 | Whitman et al. |
| 2013/0119109 A1 | 5/2013 | Farascioni et al. |
| 2013/0146641 A1 | 6/2013 | Shelton, IV et al. |
| 2013/0146642 A1 | 6/2013 | Shelton, IV et al. |
| 2013/0153636 A1 | 6/2013 | Shelton, IV et al. |
| 2013/0153641 A1 | 6/2013 | Shelton, IV et al. |
| 2013/0161374 A1 | 6/2013 | Swayze et al. |
| 2013/0175316 A1 | 7/2013 | Thompson et al. |
| 2013/0193188 A1 | 8/2013 | Shelton, IV et al. |
| 2013/0256380 A1 | 10/2013 | Schmid et al. |
| 2013/0277410 A1 | 10/2013 | Fernandez et al. |
| 2013/0334280 A1 | 12/2013 | Krehel et al. |
| 2014/0014704 A1 | 1/2014 | Onukuri et al. |
| 2014/0014707 A1 | 1/2014 | Onukuri et al. |
| 2014/0021242 A1 | 1/2014 | Hodgkinson et al. |
| 2014/0048580 A1 | 2/2014 | Merchant et al. |
| 2014/0061280 A1 | 3/2014 | Ingmanson et al. |
| 2014/0076955 A1 | 3/2014 | Lorenz |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0166720 A1 | 6/2014 | Chowaniec et al. |
| 2014/0166721 A1 | 6/2014 | Stevenson et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175146 A1 | 6/2014 | Knodel |
| 2014/0175150 A1 | 6/2014 | Shelton, IV et al. |
| 2014/0203062 A1 | 7/2014 | Viola |
| 2014/0239036 A1 | 8/2014 | Zerkle et al. |
| 2014/0239037 A1 | 8/2014 | Boudreaux et al. |
| 2014/0239038 A1 | 8/2014 | Leimbach et al. |
| 2014/0239040 A1 | 8/2014 | Fanelli et al. |
| 2014/0239041 A1 | 8/2014 | Zerkle et al. |
| 2014/0239043 A1 | 8/2014 | Simms et al. |
| 2014/0239044 A1 | 8/2014 | Hoffman |
| 2014/0239047 A1 | 8/2014 | Hodgkinson et al. |
| 2014/0246471 A1 | 9/2014 | Jaworek et al. |
| 2014/0246472 A1 | 9/2014 | Kimsey et al. |
| 2014/0246475 A1 | 9/2014 | Hall et al. |
| 2014/0246478 A1 | 9/2014 | Baber et al. |
| 2014/0252062 A1 | 9/2014 | Mozdzierz |
| 2014/0252064 A1 | 9/2014 | Mozdzierz et al. |
| 2014/0252065 A1 | 9/2014 | Hessler et al. |
| 2014/0263539 A1 | 9/2014 | Leimbach et al. |
| 2014/0263540 A1 | 9/2014 | Covach et al. |
| 2014/0263541 A1 | 9/2014 | Leimbach et al. |
| 2014/0263542 A1 | 9/2014 | Leimbach et al. |
| 2014/0263544 A1 | 9/2014 | Ranucci et al. |
| 2014/0263546 A1 | 9/2014 | Aranyi |
| 2014/0263550 A1 | 9/2014 | Aranyi et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263557 A1 | 9/2014 | Schaller |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263570 A1 | 9/2014 | Hopkins et al. |
| 2014/0284371 A1 | 9/2014 | Morgan et al. |
| 2014/0291379 A1 | 10/2014 | Schellin et al. |
| 2014/0291380 A1 | 10/2014 | Weaner et al. |
| 2014/0291383 A1 | 10/2014 | Spivey et al. |
| 2014/0303668 A1 | 10/2014 | Nicholas et al. |
| 2014/0309665 A1 | 10/2014 | Parihar et al. |
| 2014/0332578 A1 | 11/2014 | Fernandez et al. |
| 2014/0339286 A1 | 11/2014 | Motooka et al. |
| 2014/0353358 A1 | 12/2014 | Shelton, IV et al. |
| 2014/0367445 A1 | 12/2014 | Ingmanson et al. |
| 2014/0367446 A1 | 12/2014 | Ingmanson et al. |
| 2015/0048143 A1 | 2/2015 | Scheib et al. |
| 2015/0053740 A1 | 2/2015 | Shelton, IV |
| 2015/0053742 A1 | 2/2015 | Shelton, IV et al. |
| 2015/0053744 A1 | 2/2015 | Swayze et al. |
| 2015/0060517 A1 | 3/2015 | Williams |
| 2015/0076205 A1 | 3/2015 | Zergiebel |
| 2015/0076211 A1 | 3/2015 | Irka et al. |
| 2015/0080912 A1 | 3/2015 | Sapre |
| 2015/0133996 A1 | 5/2015 | Shelton, IV et al. |
| 2015/0134076 A1 | 5/2015 | Shelton, IV et al. |
| 2015/0150556 A1 | 6/2015 | McCuen |
| 2015/0157321 A1 | 6/2015 | Zergiebel et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173748 A1 | 6/2015 | Marczyk et al. |
| 2015/0173749 A1 | 6/2015 | Shelton, IV et al. |
| 2015/0173750 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0182220 A1 | 7/2015 | Yates et al. |
| 2015/0209040 A1 | 7/2015 | Whitman et al. |
| 2015/0250474 A1 | 9/2015 | Abbott et al. |
| 2015/0297225 A1 | 10/2015 | Huitema et al. |
| 2015/0316431 A1 | 11/2015 | Collins et al. |
| 2015/0351765 A1 | 12/2015 | Valentine et al. |
| 2015/0359534 A1 | 12/2015 | Gibbons, Jr. |
| 2015/0366560 A1 | 12/2015 | Chen et al. |
| 2015/0374371 A1 | 12/2015 | Richard et al. |
| 2015/0374372 A1 | 12/2015 | Zergiebel et al. |
| 2015/0374376 A1 | 12/2015 | Shelton, IV |
| 2016/0030040 A1 | 2/2016 | Calderoni et al. |
| 2016/0051259 A1 | 2/2016 | Hopkins et al. |
| 2016/0058443 A1 | 3/2016 | Yates et al. |
| 2016/0066907 A1 | 3/2016 | Cheney et al. |
| 2016/0067074 A1 | 3/2016 | Thompson et al. |
| 2016/0089137 A1 | 3/2016 | Hess et al. |
| 2016/0095585 A1 | 4/2016 | Zergiebel et al. |
| 2016/0100835 A1 | 4/2016 | Linder et al. |
| 2016/0106406 A1 | 4/2016 | Cabrera et al. |
| 2016/0113647 A1 | 4/2016 | Hodgkinson |
| 2016/0113648 A1 | 4/2016 | Zergiebel et al. |
| 2016/0113649 A1 | 4/2016 | Zergiebel et al. |
| 2016/0120542 A1 | 5/2016 | Westling et al. |
| 2016/0166249 A1 | 6/2016 | Knodel |
| 2016/0166253 A1 | 6/2016 | Knodel |
| 2016/0199064 A1 | 7/2016 | Shelton, IV et al. |
| 2016/0199084 A1 | 7/2016 | Takei |
| 2016/0206315 A1 | 7/2016 | Olson |
| 2016/0206336 A1 | 7/2016 | Frushour |
| 2016/0235494 A1 | 8/2016 | Shelton, IV et al. |
| 2016/0242773 A1 | 8/2016 | Sadowski et al. |
| 2016/0242774 A1 | 8/2016 | Ebner |
| 2016/0242779 A1 | 8/2016 | Aranyi et al. |
| 2016/0249915 A1 | 9/2016 | Beckman et al. |
| 2016/0249916 A1 | 9/2016 | Shelton, IV et al. |
| 2016/0249918 A1 | 9/2016 | Shelton, IV et al. |
| 2016/0249927 A1 | 9/2016 | Beckman et al. |
| 2016/0249929 A1 | 9/2016 | Cappola et al. |
| 2016/0249945 A1 | 9/2016 | Shelton, IV et al. |
| 2016/0256071 A1 | 9/2016 | Shelton, IV et al. |
| 2016/0256152 A1 | 9/2016 | Kostrzewski |
| 2016/0256154 A1 | 9/2016 | Shelton, IV et al. |
| 2016/0256160 A1 | 9/2016 | Shelton, IV et al. |
| 2016/0256161 A1 | 9/2016 | Overmyer |
| 2016/0256162 A1 | 9/2016 | Shelton, IV et al. |
| 2016/0256163 A1 | 9/2016 | Shelton, IV et al. |
| 2016/0256184 A1 | 9/2016 | Shelton, IV et al. |
| 2016/0256185 A1 | 9/2016 | Shelton, IV et al. |
| 2016/0256187 A1 | 9/2016 | Shelton, IV et al. |
| 2016/0262750 A1 | 9/2016 | Hausen et al. |
| 2016/0270783 A1 | 9/2016 | Yigit et al. |

(56) References Cited

U.S. PATENT DOCUMENTS

| | | |
|---|---|---|
| 2016/0270788 A1 | 9/2016 | Czernik |
| 2016/0278764 A1 | 9/2016 | Shelton, IV et al. |
| 2016/0278765 A1 | 9/2016 | Shelton, IV et al. |
| 2016/0278771 A1 | 9/2016 | Shelton, IV et al. |
| 2016/0278774 A1 | 9/2016 | Shelton, IV et al. |
| 2016/0278775 A1 | 9/2016 | Shelton, IV et al. |
| 2016/0278777 A1 | 9/2016 | Shelton, IV et al. |
| 2016/0278848 A1 | 9/2016 | Boudreaux et al. |
| 2016/0287250 A1 | 10/2016 | Shelton, IV et al. |
| 2016/0287251 A1 | 10/2016 | Shelton, IV et al. |
| 2016/0296216 A1 | 10/2016 | Nicholas et al. |
| 2016/0296226 A1 | 10/2016 | Kostrzewski |
| 2016/0302791 A1 | 10/2016 | Schmitt |
| 2016/0310134 A1 | 10/2016 | Contini et al. |
| 2016/0324514 A1 | 11/2016 | Srinivas et al. |
| 2016/0324518 A1 | 11/2016 | Nicholas et al. |
| 2016/0338703 A1 | 11/2016 | Scirica et al. |
| 2016/0345971 A1* | 12/2016 | Bucciaglia ....... A61B 17/07207 |
| 2016/0345973 A1 | 12/2016 | Marczyk et al. |
| 2016/0354176 A1 | 12/2016 | Schmitt |
| 2016/0374678 A1 | 12/2016 | Becerra et al. |
| 2017/0000483 A1 | 1/2017 | Motai et al. |
| 2017/0020525 A1 | 1/2017 | Shah |
| 2017/0189023 A1 | 7/2017 | Yan |
| 2018/0235609 A1* | 8/2018 | Harris ............... A61B 17/07207 |
| 2018/0368867 A1* | 12/2018 | Bucciaglia ........... A61B 17/285 |
| 2019/0125342 A1 | 5/2019 | Beardsley et al. |

FOREIGN PATENT DOCUMENTS

| | | | |
|---|---|---|---|
| CA | 2884962 A1 | 11/2015 | |
| DE | 2744824 A1 | 4/1978 | |
| DE | 2903159 A1 | 7/1980 | |
| DE | 3114135 A1 | 10/1982 | |
| DE | 4213426 A1 | 10/1992 | |
| DE | 4300307 A1 | 7/1994 | |
| EP | 0041022 A1 | 12/1981 | |
| EP | 0136950 A2 | 4/1985 | |
| EP | 0140552 A2 | 5/1985 | |
| EP | 0156774 A2 | 10/1985 | |
| EP | 0213817 A1 | 3/1987 | |
| EP | 0216532 A1 | 4/1987 | |
| EP | 0220029 A1 | 4/1987 | |
| EP | 0273468 A2 | 7/1988 | |
| EP | 0324166 A2 | 7/1989 | |
| EP | 0324635 A1 | 7/1989 | |
| EP | 0324637 A1 | 7/1989 | |
| EP | 0324638 A1 | 7/1989 | |
| EP | 0365153 A1 | 4/1990 | |
| EP | 0369324 A1 | 5/1990 | |
| EP | 0373762 A1 | 6/1990 | |
| EP | 0380025 A2 | 8/1990 | |
| EP | 0399701 A1 | 11/1990 | |
| EP | 0449394 A2 | 10/1991 | |
| EP | 0484677 A1 | 5/1992 | |
| EP | 0489436 A1 | 6/1992 | |
| EP | 0503662 A1 | 9/1992 | |
| EP | 0514139 A2 | 11/1992 | |
| EP | 0536903 A2 | 4/1993 | |
| EP | 0537572 A2 | 4/1993 | |
| EP | 0539762 A1 | 5/1993 | |
| EP | 0545029 A1 | 6/1993 | |
| EP | 0552050 A2 | 7/1993 | |
| EP | 0552423 A2 | 7/1993 | |
| EP | 0579038 A1 | 1/1994 | |
| EP | 0589306 A2 | 3/1994 | |
| EP | 0591946 A1 | 4/1994 | |
| EP | 0592243 A2 | 4/1994 | |
| EP | 0593920 A1 | 4/1994 | |
| EP | 0598202 A1 | 5/1994 | |
| EP | 0598579 A1 | 5/1994 | |
| EP | 0600182 A2 | 6/1994 | |
| EP | 0621006 A1 | 10/1994 | |
| EP | 0621009 A1 | 10/1994 | |
| EP | 0656188 A2 | 6/1995 | |
| EP | 0666057 A2 | 8/1995 | |
| EP | 0705571 A1 | 4/1996 | |
| EP | 0760230 A1 | 3/1997 | |
| EP | 1952769 A2 | 8/2008 | |
| EP | 2090253 A2 | 8/2009 | |
| EP | 2090254 A1 | 8/2009 | |
| EP | 2583630 A2 | 4/2013 | |
| EP | 2586382 A2 | 5/2013 | |
| EP | 2907456 A1 | 8/2015 | |
| FR | 391239 A | 10/1908 | |
| FR | 2542188 A1 | 9/1984 | |
| FR | 2660851 A1 | 10/1991 | |
| FR | 2681775 A1 | 4/1993 | |
| GB | 1352554 A | 5/1974 | |
| GB | 1452185 A | 10/1976 | |
| GB | 1555455 A | 11/1979 | |
| GB | 2048685 A | 12/1980 | |
| GB | 2070499 A | 9/1981 | |
| GB | 2141066 A | 12/1984 | |
| GB | 2165559 A | 4/1986 | |
| JP | 51149985 | 12/1976 | |
| JP | 2001087272 | 4/2001 | |
| SU | 659146 A1 | 4/1979 | |
| SU | 728848 A1 | 4/1980 | |
| SU | 980703 A1 | 12/1982 | |
| SU | 990220 A1 | 1/1983 | |
| WO | 2008302247 | 7/1983 | |
| WO | 8910094 A1 | 11/1989 | |
| WO | 9210976 A1 | 7/1992 | |
| WO | 9308754 A1 | 5/1993 | |
| WO | 9314706 A1 | 8/1993 | |
| WO | 2004/032760 A2 | 4/2004 | |
| WO | 2009071070 A2 | 6/2009 | |
| WO | 20150191887 A1 | 12/2015 | |

OTHER PUBLICATIONS

Partial European Search Report issued in EP Application No. 21154211.3, dated Mar. 26, 2021.

* cited by examiner

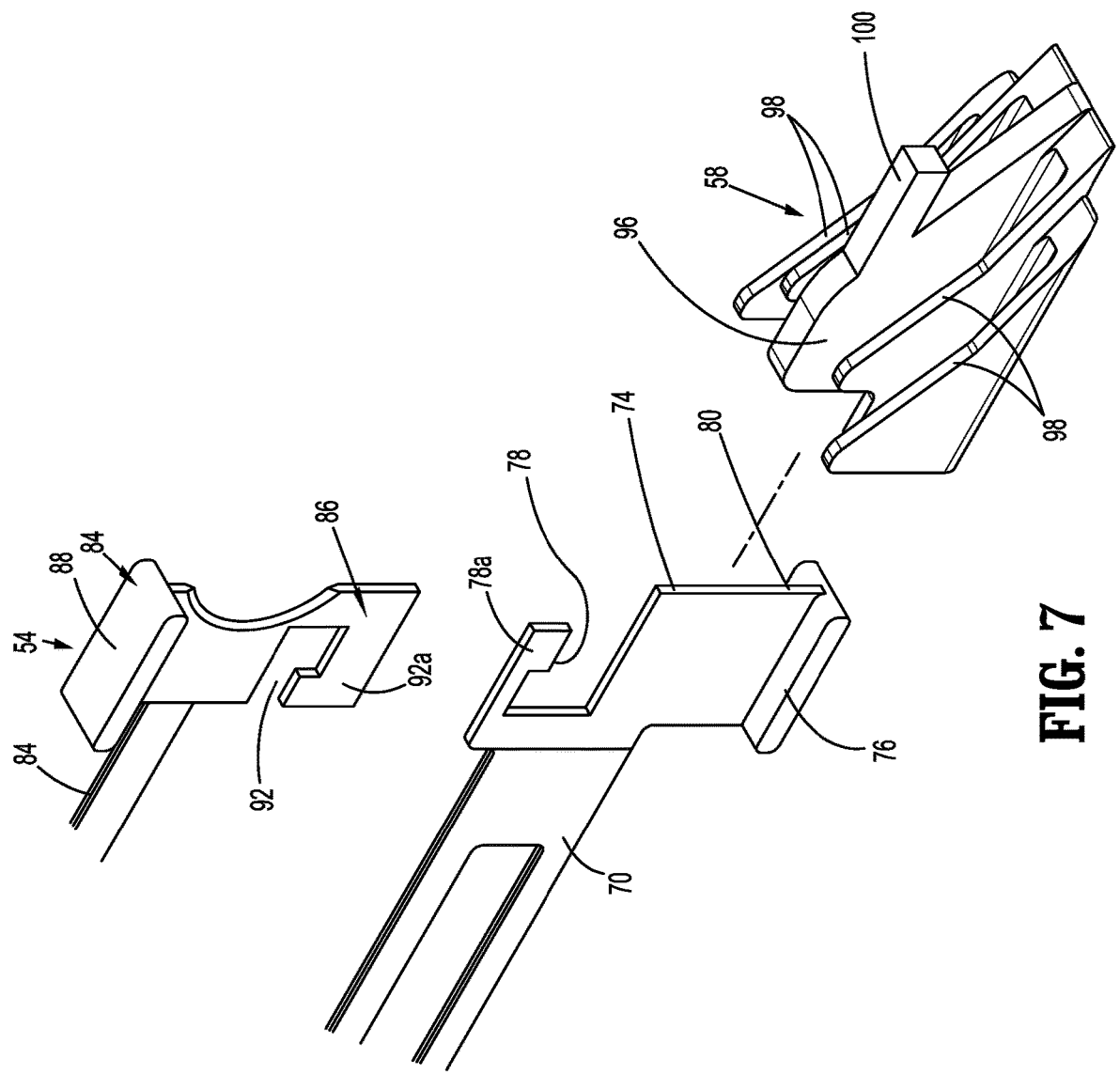

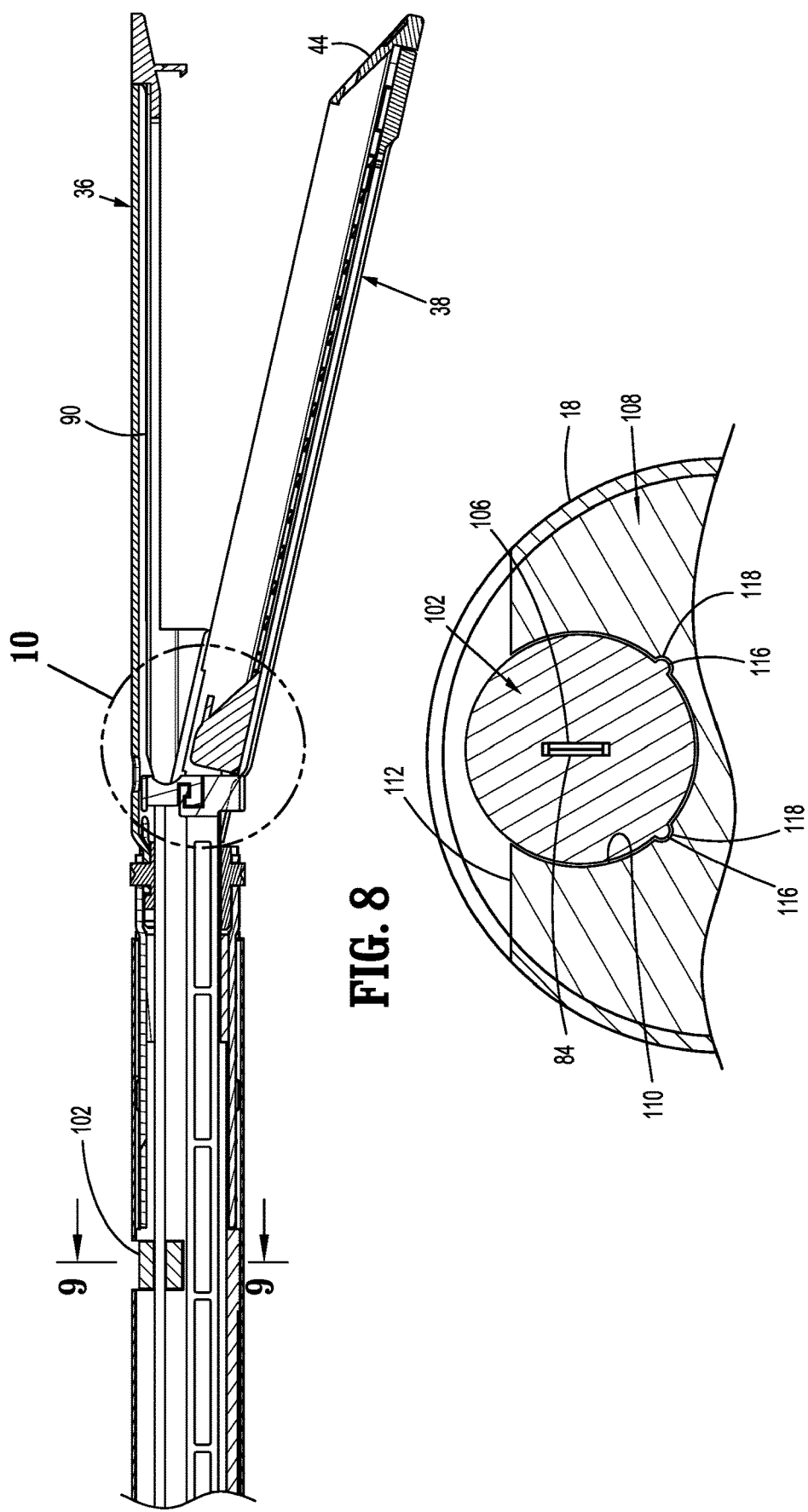

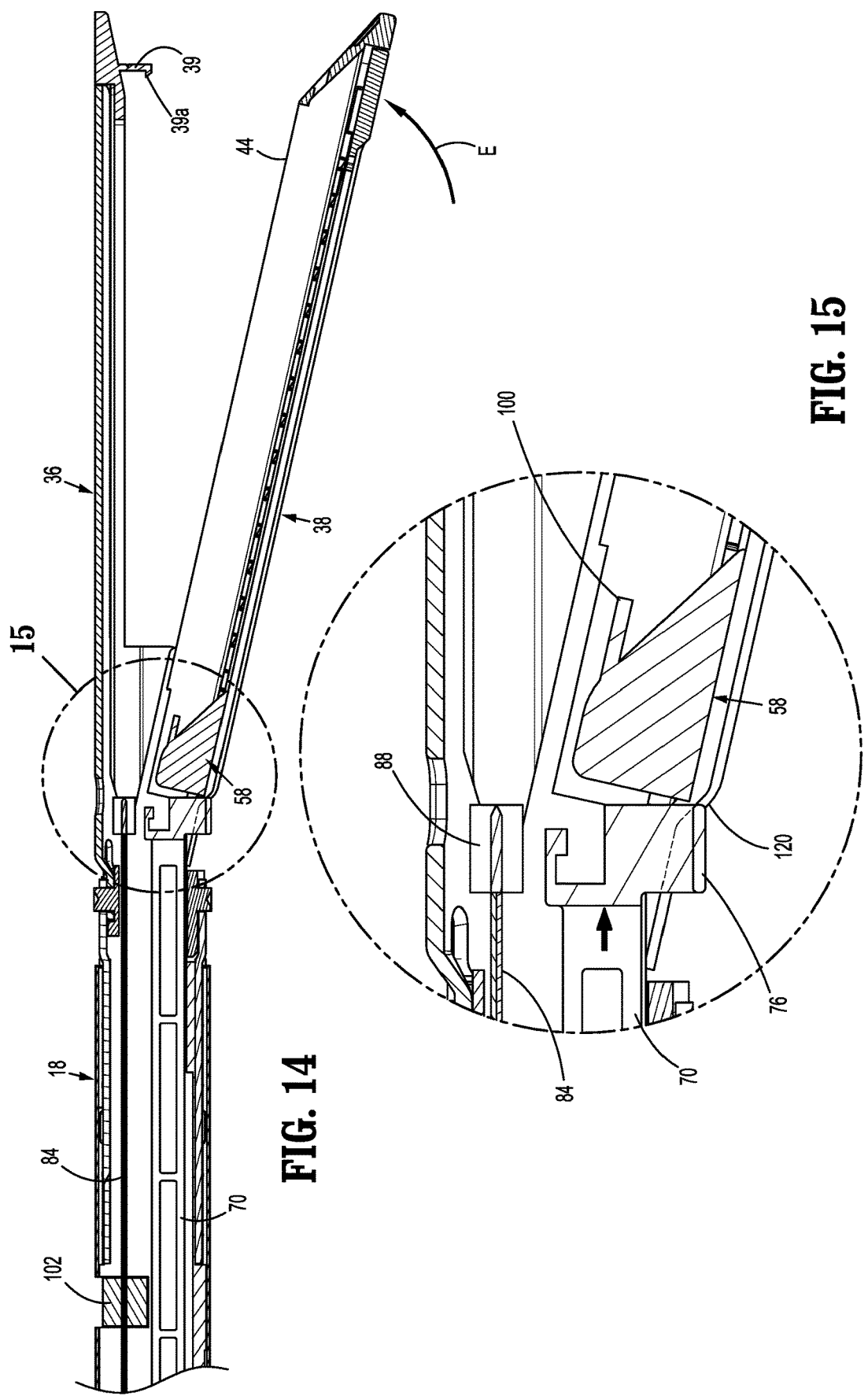

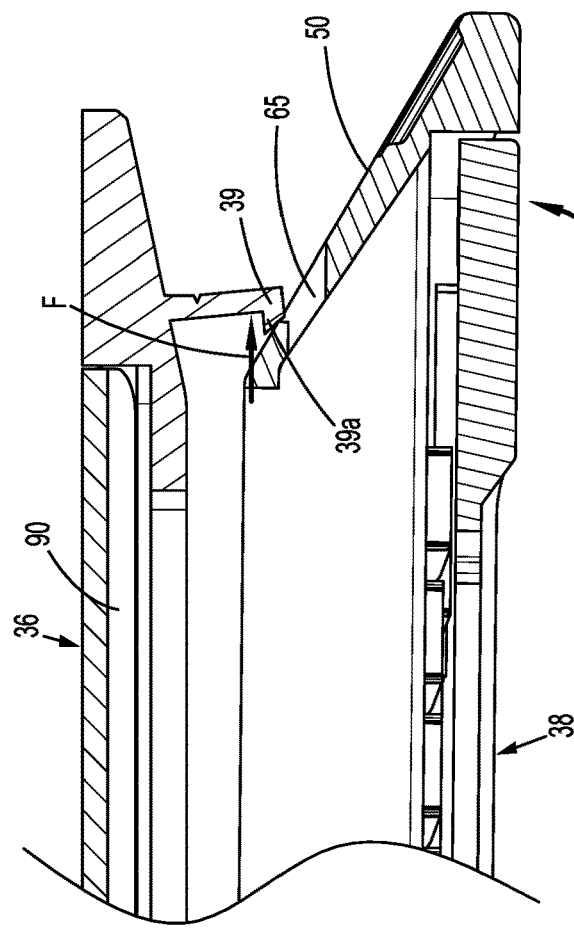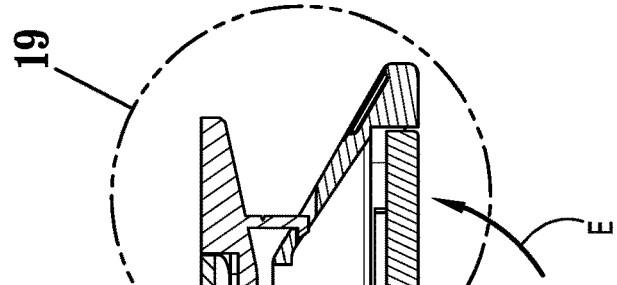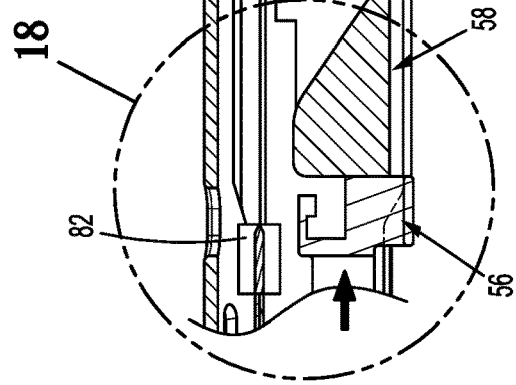
FIG. 16
FIG. 17

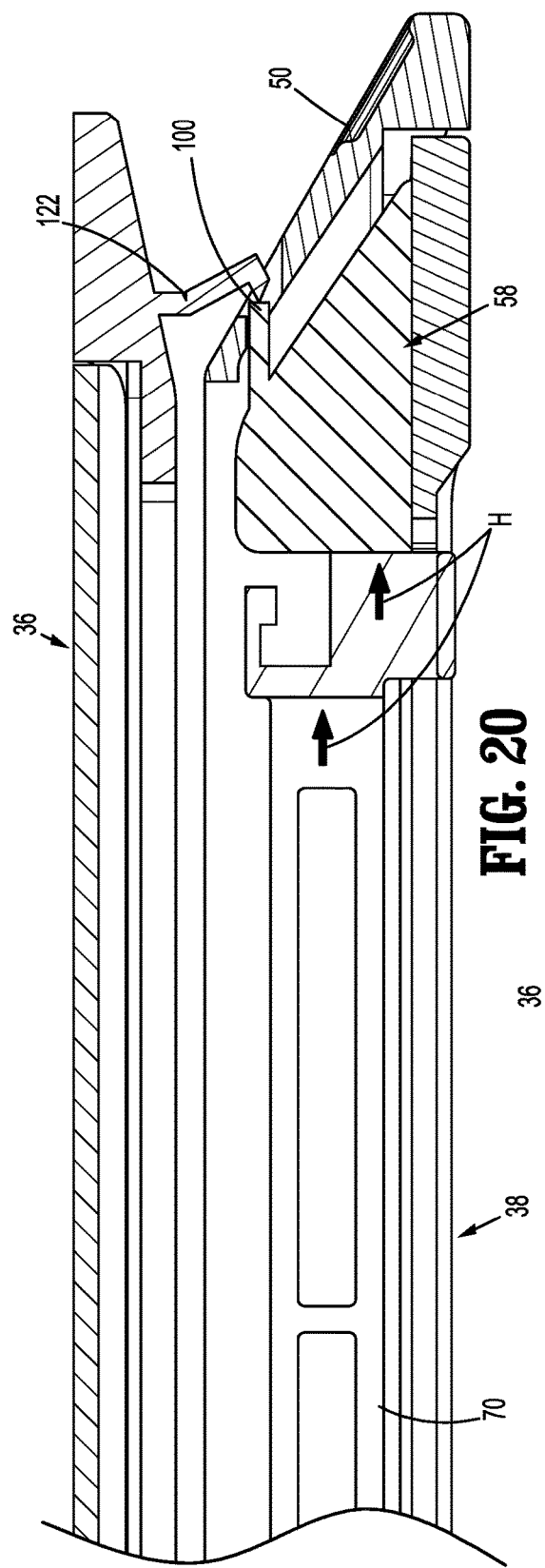

STAPLING DEVICE WITH SELECTIVE CUTTING

FIELD

This disclosure is directed to a surgical stapling device and, more particularly, to a linear surgical stapling device having a tool assembly that can selectively be operated in a cutting mode or a non-cutting mode.

BACKGROUND

Surgical stapling devices are commonly used during a variety of surgical procedures to staple and/or cut tissue. Stapling and cutting of tissue can be accomplished more quickly using surgical stapling devices than can be accomplished using traditional suturing techniques. In addition, endoscopic stapling devices can be used to perform less invasive surgical procedures than possible using traditional suturing techniques. As such, the use of surgical stapling devices to perform certain surgical procedures to reduce patient trauma and improve patient recovery times is desirable.

Typically, linear endoscopic surgical stapling devices include a tool assembly that includes a staple cartridge and an anvil assembly that are movable in relation to each other between open and clamped positions. The staple cartridge defines a plurality of staple pockets that receive staples and the anvil assembly defines a plurality of staple deforming pockets. When the tool assembly is in the clamped position, the staple deforming pockets of the anvil assembly are aligned with the staple pockets of the staple cartridge such that legs of the staples are received and deformed within the staple deforming pockets when the stapling device is fired. The staple cartridge and the anvil assembly must be properly aligned to effect proper staple formation.

Generally, the staple cartridge and the anvil assembly have proximal ends that are secured to each other by a pivot member such that the staple cartridge and the anvil assembly can be pivoted from the open position in which distal ends of the staple cartridge and the anvil assembly are spaced from each other to the clamped position in which the staple cartridge and the anvil assembly are in juxtaposed alignment. During firing of the staples from the staple cartridge, forces on the staple cartridge and the anvil assembly for firing the staples tend to deflect the staple cartridge and anvil assembly outwardly away from each other. In certain stapling devices, a knife bar is provided that includes upper and lower beams that engage the anvil assembly and staple cartridge to minimize deflection of the anvil and cartridge assemblies during firing. In stapling devices that do not include a knife bar, deflection of the anvil and cartridge assemblies may have a detrimental effect on staple formation.

SUMMARY

One aspect of the disclosure is directed to a tool assembly including an anvil, a cartridge assembly, a drive assembly, and a knife assembly. The anvil defines an anvil channel and a knife slot that communicates with the anvil channel. The cartridge assembly includes a channel member and a staple cartridge. The channel member is configured to receive the staple cartridge and defines a longitudinal slot. The staple cartridge supports a plurality of staples and defines a knife slot that is aligned with the longitudinal slot. The drive assembly includes a resilient beam and a working member having a first beam and a first vertical strut. The vertical strut includes first engagement structure. The knife bar assembly includes a knife bar and a flexible drive member. The knife bar includes a second beam and a second vertical strut that supports a knife and includes second engagement structure that is adapted to be coupled to the first engagement structure to couple the drive assembly to the knife bar assembly such that movement of the drive assembly in relation to the anvil and cartridge assembly causes corresponding movement of the knife bar assembly in relation to the anvil and cartridge assembly. The knife bar assembly is rotatable between a first position in which the first and second engagement structures are coupled together and a second position in which the first and second engagement structures are uncoupled.

In embodiments, one of the anvil and the cartridge assembly includes a distal portion having a locking member that is configured to engage the other of the anvil and cartridge assembly to secure the distal portions of the anvil and cartridge assembly together and define a maximum tissue gap between the anvil and the cartridge assembly during firing of the tool assembly.

In some embodiments, the locking member includes a hook portion that is supported on the distal portion of the anvil and the staple cartridge defines an opening that receives the hook portion when the tool assembly is moved to a clamped position to secure the distal portion of the anvil to the distal portion of the cartridge assembly.

In certain embodiments, the second beam is received with the anvil channel and the second vertical strut extends through the knife slot of the anvil when the knife bar assembly is in the first position and is advanced within the tool assembly.

In embodiments, the first engagement structure includes a first L-shaped slot and the second engagement structure includes a first L-shaped leg, wherein the first L-shaped leg is received within the first L-shaped slot when the knife bar assembly is in the first position.

In some embodiments, the first engagement structure includes a first L-shaped slot and a first L-shaped leg and the second engagement structure includes a second L-shaped leg and a second L-shaped slot, wherein the first L-shaped leg is received within the first L-shaped slot and the second L-shaped leg is received within the second L-shaped slot when the knife bar assembly is in the first position.

Another aspect of the present disclosure is directed to a stapling device including an elongate body and a tool assembly. The elongate body has a proximal portion and a distal portion. The tool assembly is supported on the distal portion of the elongate body and includes an anvil, a cartridge assembly, a drive assembly, and a knife bar assembly. The anvil defines an anvil channel and a knife slot that communicates with the anvil channel. The cartridge assembly includes a channel member and a staple cartridge. The channel member is configured to receive the staple cartridge and defines a longitudinal slot. The staple cartridge supports a plurality of staples and defines a knife slot that is aligned with the longitudinal slot. The drive assembly includes a resilient beam and a working member having a first beam and a first vertical strut. The first vertical strut includes first engagement structure. The knife bar assembly includes a knife bar and a flexible drive member. The knife bar includes a second beam and a second vertical strut. The second vertical strut supports a knife and includes second engagement structure that is adapted to be coupled to the first engagement structure to couple the drive assembly to the knife bar assembly such that movement of the drive assembly in relation to the anvil and cartridge assembly causes corresponding movement of the knife bar assembly in relation to the anvil and cartridge assembly. The knife bar assembly is rotatable between a first position in which the first and second engagement structures are coupled together and a second position in which the first and second engagement structures are uncoupled.

In embodiments, a control knob is supported on the stapling device proximally of the tool assembly. The control knob is secured to the flexible drive member of the knife bar assembly and is rotatable to cause rotation of the knife bar assembly between the first position and the second position.

In some embodiments, the control knob is supported on the elongate body at a location accessible to a clinician.

In certain embodiments, the elongate body includes an inner housing portion that defines a cylindrical cavity that receives the control knob, wherein the control knob does not extend outwardly of an outer diameter of the elongate body.

In embodiments, the control knob includes first and second protrusions and the inner housing portion of the elongate body includes at least one recess positioned to receive the first and second protrusions to retain the control knob in the first and second positions, respectively.

Another aspect of the disclosure is directed to a tool assembly including an anvil, a cartridge assembly, a drive assembly, and a locking member. The anvil defines an anvil channel and a knife slot that communicates with the anvil channel. The cartridge assembly includes a channel member and a staple cartridge. The channel member is configured to receive the staple cartridge and defines a longitudinal slot. The staple cartridge supports a plurality of staples and defines a knife slot that is aligned with the longitudinal slot. The drive assembly includes a resilient beam and a working member having a first beam and a first vertical strut. The first vertical strut includes first engagement structure. The locking member is supported on a distal portion of one of the anvil and the cartridge assembly and is configured to engage the other of the anvil and cartridge assembly to secure the distal portion of the anvil to the distal portion of the cartridge assembly and define a maximum tissue gap between the anvil and the cartridge assembly during firing of the tool assembly.

BRIEF DESCRIPTION OF THE DRAWINGS

Various embodiments of the disclosed surgical stapling device are described herein below with reference to the drawings, wherein:

FIG. 7 is an enlarged view of the indicated area of detail shown in FIG. 6;

FIG. 8 is a cross-sectional view taken along section line 8-8 in FIG. 1;

FIG. 9 is a cross-sectional view taken along section line 9-9 of FIG. 8;

FIG. 14 is a side cross-sectional view of the distal portion of the reload assembly shown in FIG. 2 with the knife of the clamp and knife assembly disengaged from the clamp of the clamp and knife assembly;

FIG. 15 is an enlarged view of the indicated area of detail shown in FIG. 14;

FIG. 16 is a cross-sectional view of a distal portion of the tool assembly of the stapling device shown in FIG. 1 as the tool assembly is moved to the clamped position;

FIG. 17 is a cross-sectional view of the tool assembly of the surgical stapling device shown in FIG. 1 with the tool assembly in a clamped position as the clamp member begins to move from a retracted position towards an advanced position disengaged with the knife assembly;

FIG. 20 is a cross-sectional view of the distal portion of the tool assembly of the stapling device shown in FIG. 1 as the clamp member is moved to its advanced position with the tool assembly in the clamped position;

FIG. 21 is a cross-sectional view of the distal portion of the tool assembly of the stapling device shown in FIG. 1 with the clamp member in its advanced position and the tool assembly unlocked as the tool assembly moves towards the open position;

DETAILED DESCRIPTION OF EMBODIMENTS

Figure 1:
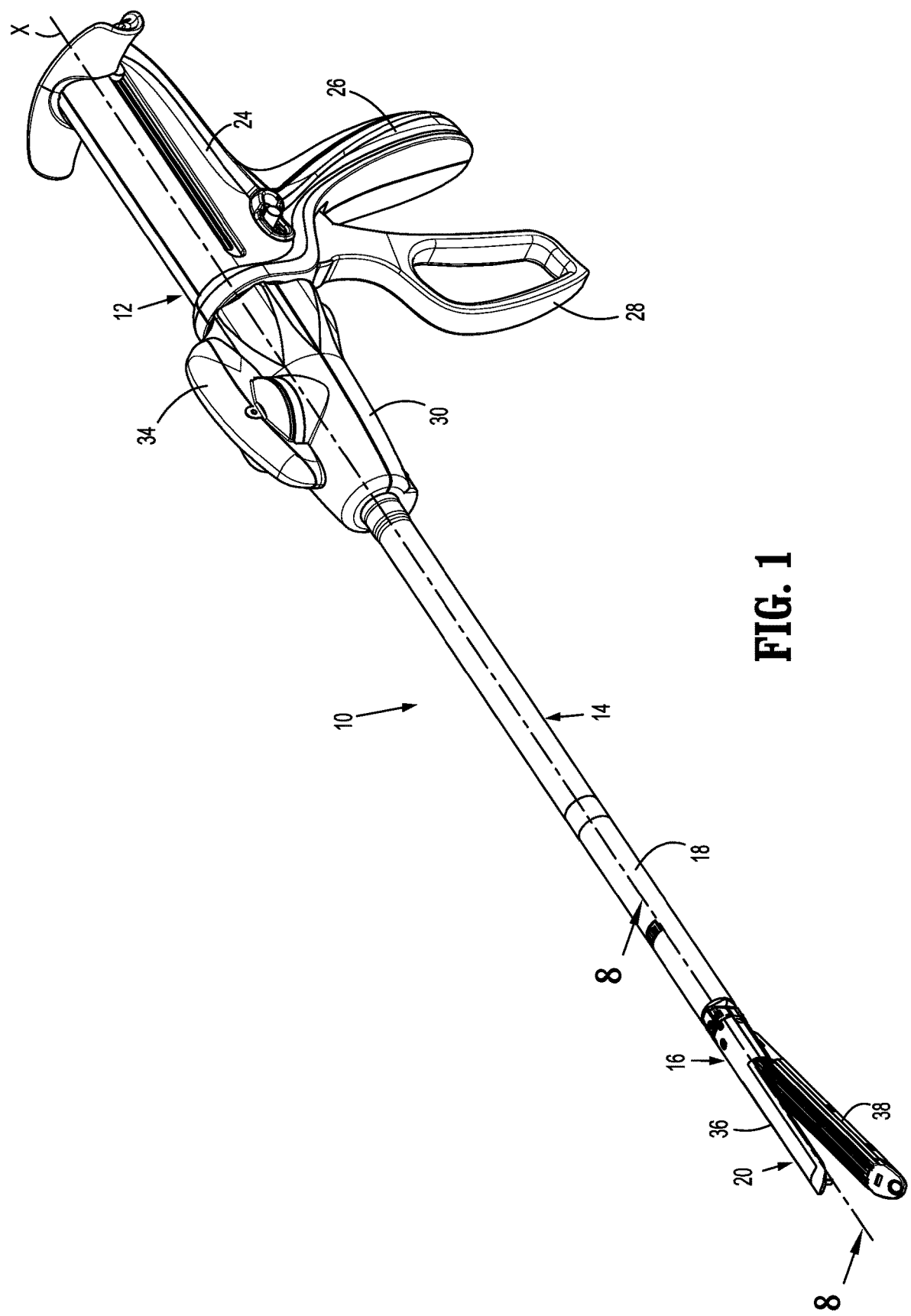
FIG. 1 is a side perspective top view of an exemplary embodiment of the disclosed surgical stapling device with a tool assembly of the stapling device in an open condition.

The disclosed stapling device will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. Further, the term "clinician" is used generally to refer to medical personnel including doctors, nurses, and support personnel.

In FIG. 1, the surgical stapling device is illustrated generally as stapling device 10 and includes a handle assembly 12, an elongate body 14, and a staple reload 16. The elongate body 14 defines a longitudinal axis "X" and includes a proximal portion that is coupled to the handle assembly 12 and a distal portion that supports the staple reload 16. The staple reload 16 includes a proximal body portion 18 and a tool assembly 20 supported on the proximal body portion 18. The proximal body portion 18 is releasably coupled to the distal portion of the elongate body 14. Alternately, the staple reload 16 and the elongate body 14 can be integrally formed such that the tool assembly 20 is fixedly attached to the elongate body 14.

The handle assembly 12 includes a housing 24 that defines a stationary handgrip 26 and supports a movable trigger 28 and a rotation knob 30. The rotation knob 30 is coupled to a distal portion of the housing 24 for rotation and supports the elongate body 14 such that rotation of the rotation knob 30 causes rotation of the elongate body 14 about the longitudinal axis "X". The movable trigger 28 is supported by the housing 24 and can be pivoted in relation to the stationary handgrip 26 to actuate the tool assembly 20. In embodiments, the rotation knob 30 also supports an articulation knob 34 that can pivot or rotate about an axis perpendicular to the longitudinal axis "X" to articulate the tool assembly 20 from a position aligned with the longitudinal axis "X" to positions misaligned with the longitudinal axis "X". Although illustrated as being a manually operated handle assembly 12, it is envisioned that the handle assembly 12 may be electrically or pneumatically powered, and may be adapted for use or coupled to a robotic surgical system.

Figure 2:
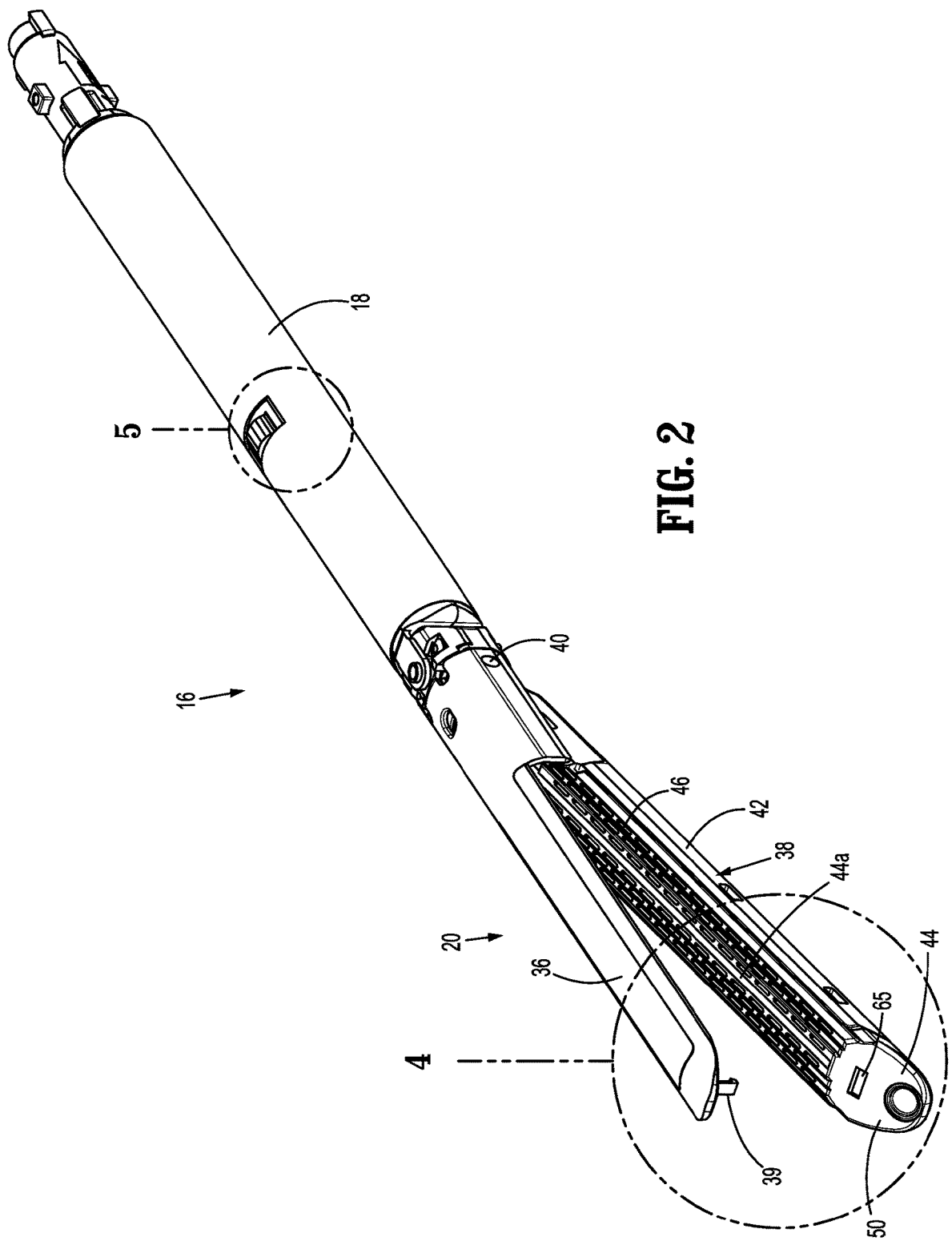
FIG. 2 is a side perspective top view of a reload assembly of the surgical stapling device shown in FIG. 1 with the tool assembly in the open condition.
Figure 3:
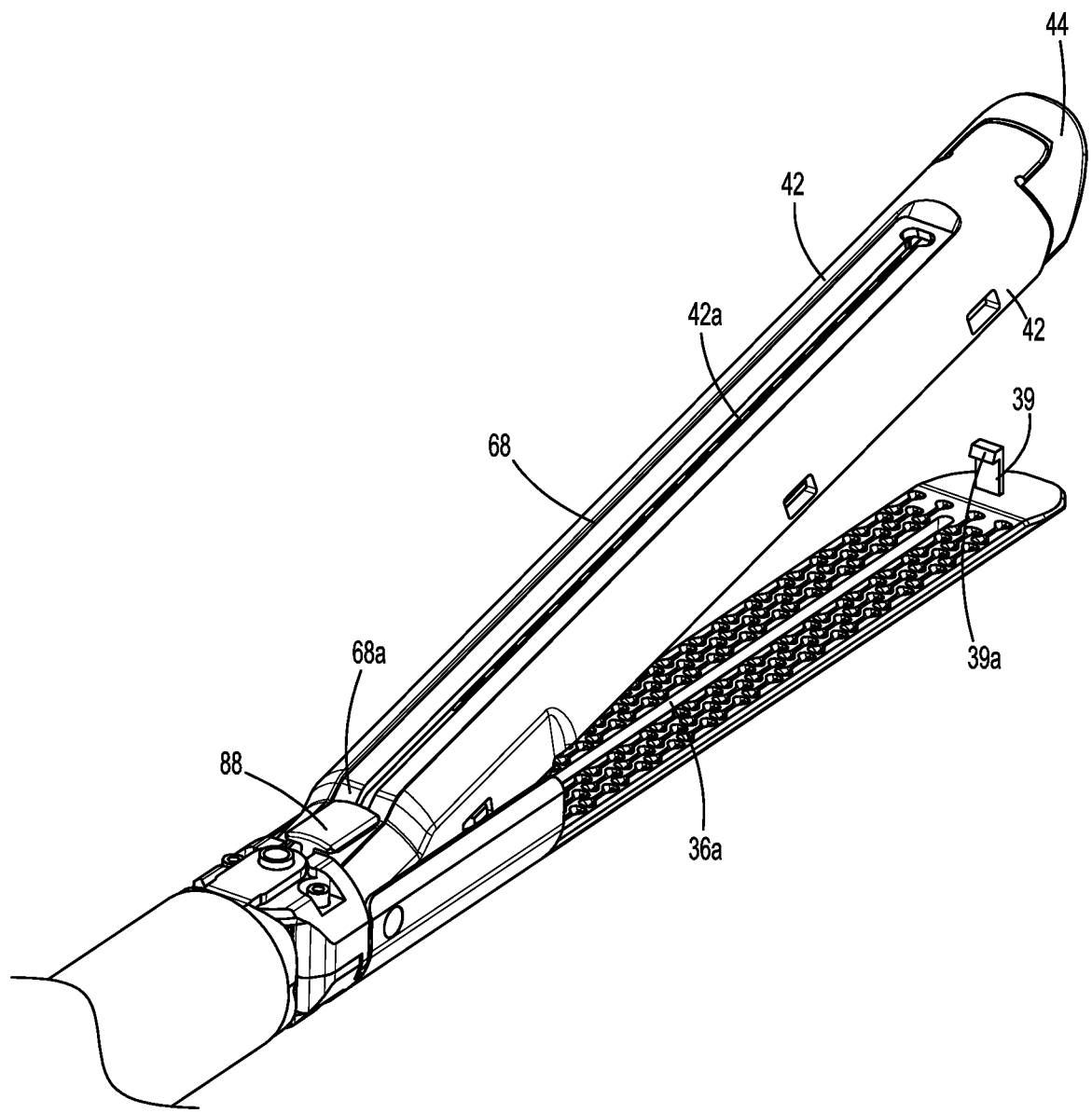
FIG. 3 is a side perspective bottom view of the tool assembly of the stapling device shown in FIG. 2 from FIG. 4 is an enlarged view of the indicated area of detail shown in FIG. 2.

FIGS. 2-7 illustrate the tool assembly 20 which includes an anvil 36 and a cartridge assembly 38. The anvil 36 and the cartridge assembly 38 each include a distal portion and a proximal portion. The proximal portion of the anvil 36 is coupled to the proximal portion of the cartridge assembly 38 by a pivot member 40 such that the tool assembly 20 can pivot between an open position (FIG. 14) in which the distal portions of the anvil 36 and the cartridge assembly 38 are spaced from each other and a clamped position (FIG. 17) in which the anvil 36 and cartridge assembly 38 are in juxtaposed alignment. The distal portion of the anvil 36 supports a flexible locking member 39 that includes a hook portion 39a which is described in further detail below. The anvil 36 includes a tissue engaging surface that defines a longitudinally extending knife slot 36a (FIG. 3).

In embodiments, the cartridge assembly 38 includes a channel member 42 that defines a longitudinal slot 42a (FIG. 3) and a staple cartridge 44 having a tissue contact surface 46 and a knife slot 44a (FIG. 2) that is aligned with the longitudinal slot 42a formed in the channel member 42. The staple cartridge 44 defines a plurality of staple pockets 48 and is received within the channel member 42. In some embodiments, the staple cartridge 44 is adapted to be released from the channel member 42 after firing of the stapling device 10 and replaced with a new staple cartridge 44. Each of the staple pockets 48 is configured and dimensioned to receive a staple (not shown). In embodiments, the staple cartridge 44 has a tissue guide portion 50 (FIG. 4) that is angled in a direction away from the anvil 36 in the distal direction.

Figure 4:
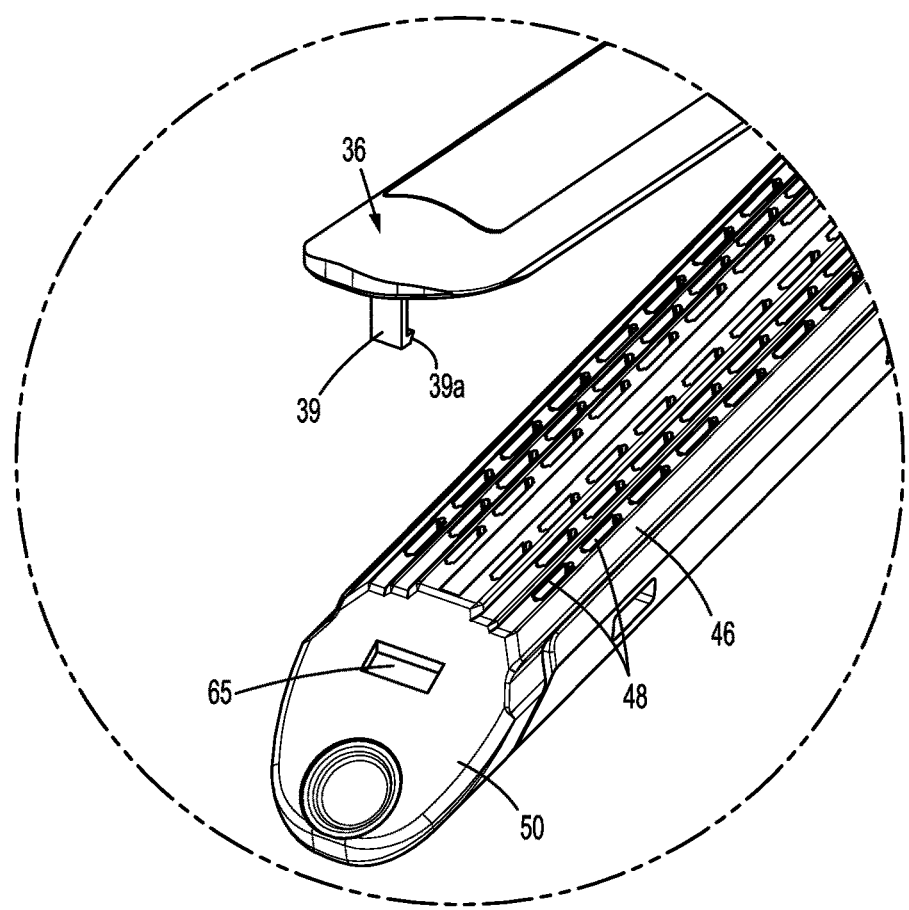
Figure 6:
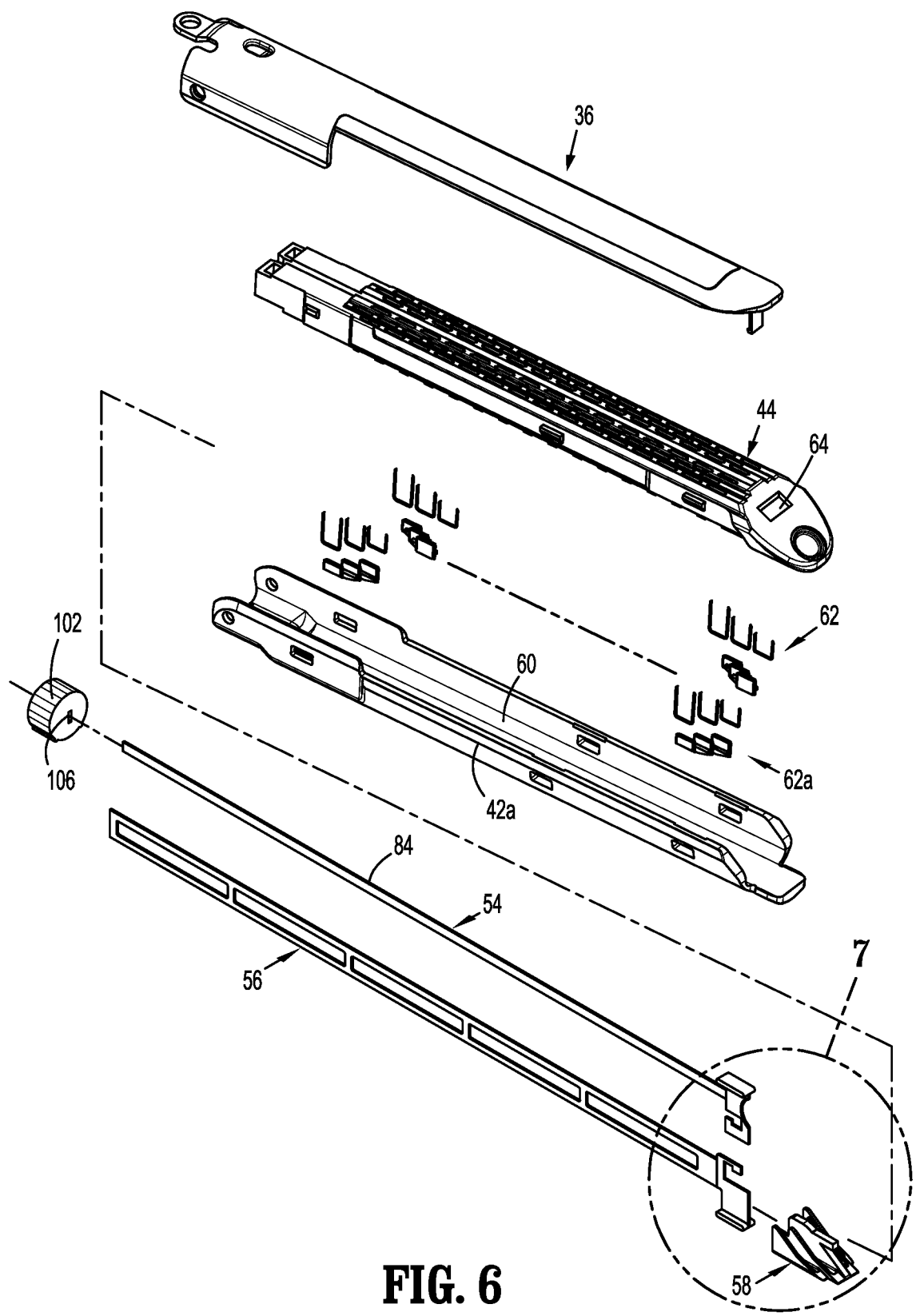
FIG. 6 is a side perspective exploded view of the tool assembly of the reload assembly shown in FIG. 2.

The cartridge assembly 38 includes the channel member 42, the staple cartridge 44 which is received within the channel member 42, a knife bar assembly 54, a drive assembly 56, and an actuation sled 58. The channel member 42 defines a recess 60 that receives the staple cartridge 44. The staple cartridge 44 supports a plurality of staples 62 and pushers 62a (FIG. 6). Each of the staples 62 is supported on a respective pusher 62a within a respective one of the staple pockets 48 (FIG. 4). In embodiments, the staple pockets 48 are aligned in three linear rows that are positioned on each side of the knife slot 44a. Alternately, the staple cartridge 44 may include one or more rows of staples 64 or other staple pocket configurations. The tissue guide portion 50 of the staple cartridge 44 defines an opening 65 that is positioned to receive the locking member 39 of the anvil 36 when the tool assembly 20 is moved to the clamped position as described in further detail below. The channel member 42 of the cartridge assembly 38 includes an outer surface 66 that defines a recess 68 (FIG. 3) and includes an angled cam surface 68a positioned at the proximal end of the recess 68. The longitudinal slot 42a is positioned within the recess 68 and is configured to receive a portion of the knife bar 54.

The drive assembly 56 includes a resilient beam 70 and a working member 72 supported on the distal end portion of the resilient beam 70. In embodiments, the resilient beam can be formed of stacked laminates although other constructions are envisioned. Although not shown, a proximal end portion of the resilient beam 70 includes a coupling member to couple the proximal end portion of the resilient beam 70 to a drive member (not shown) of the stapling device 10. A suitable coupling member is described in U.S. Pat. No. 5,865,361 and is not described in further detail in this application.

The working member 72 includes a vertical strut 74 and a lower beam 76 that extends in a direction transverse to the vertical strut 74. The lower beam 76 is received within the recess 68 defined in the outer surface 66 of the channel member 42 and the vertical strut 74 extends through the longitudinal slot 42a of the channel member 42 and the knife slot 44a of the staple cartridge 44. The vertical strut 74 defines engagement structure. In embodiments, the engagement structure includes an L-shaped slot 78 and an L-shaped leg 78a that is described in further detail below. The vertical strut 74 and the lower beam 76 define a distal surface 80 that is positioned to abut a proximal end of the actuation sled 58 such that advancement of the working member 72 through the tool assembly 20 causes advancement of the actuation sled 58 through the staple cartridge 44 to eject the staples 64 from the staple cartridge 44.

The knife bar assembly 54 includes a knife bar 82 and a flexible drive member 84. The drive member 84 may include stacked laminates although other constructions are envisioned. In embodiments, the drive member 84 may have a rectangular cross-section although other shapes are envisioned, e.g., circular. The knife bar 82 includes a vertical strut 86, and an upper beam 88. The upper beam 88 is received within an anvil channel 90 (FIG. 8) defined in the anvil 36 when the knife bar assembly 54 is advanced through the tool assembly 20. The vertical strut 86 extends through the knife slot 36a (FIG. 3) in the anvil 36 and through the knife slot 44a of the staple cartridge 44. The vertical strut 86 of the knife bar 82 defines a knife 86a and also includes engagement structure adapted to be coupled to the engagement structure of the drive assembly 56. In embodiments, the engagement structure includes an L-shaped slot 92 and an L-shaped leg 92a. The L-shaped slot 92 of the vertical strut 86 is dimensioned to receive the L-shaped leg 78a of the strut 74 and the L-shaped leg 92a of the vertical strut 86 is dimensioned to be received within the L-shaped slot 78 of the vertical strut 74 to couple the knife bar assembly 54 to the drive assembly 56 as described in further detail below.

The actuation sled 58 includes a central guide member 96 that is received within the knife slot 44a of the staple cartridge 44 and outwardly spaced cam members 98. The cam members 98 are positioned to engage the pushers 62a of the staple cartridge 44 as the actuation sled 58 is advanced through the staple cartridge 44 to eject the staples 62 from the staple cartridge 44 as is known in the art. The actuation sled 58 includes a distally extending finger 100 that is positioned to engage the flexible locking member 39 of the anvil 36 when the actuation sled 58 is in its advanced position to disengage the locking member 39 from the staple cartridge 44 as described in further detail below.

Figure 5:
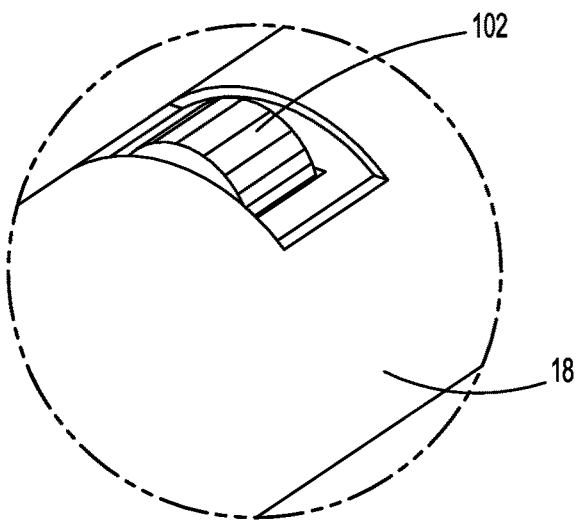
FIG. 5 is an enlarged view of the indicated area of detail shown in FIG. 2.

FIGS. 2, 5, and 6 illustrate a control knob 102 that is provided to rotate the knife bar assembly 54 into and out of engagement with the drive assembly 56. In embodiments, the control knob 102 is fixedly secured to the drive member 84 of the knife bar assembly 54 such that rotation of the control knob 102 causes corresponding rotation of the knife bar assembly 54 about an axis defined by a central axis of the control knob 102. In embodiments, the control knob 102 defines a rectangular bore 106 that receives the drive member 84 of the knife bar assembly 54 (FIG. 9) such that rotation of the control knob 102 causes rotation of the drive bar 84. In embodiments, the control knob 102 includes an outer surface that has an anti-slip configuration, e.g., ribs or knurling, to allow the control knob 102 to be rotated by a clinician with a finger, e.g., thumb or index finger. As shown, the control knob 102 may be positioned on the proximal body portion 18 of the staple reload 16. Alternately, the control knob 102 may be supported on the handle assembly 12.

FIGS. 8 and 9 illustrate the control knob 102 supported on the proximal body portion 18 of the staple reload 16. In embodiments, the proximal body portion 18 of the stapler reload 16 includes an inner housing portion 108 that defines a cylindrical bore 110 dimensioned to receive the control knob 102. The cylindrical bore 110 is positioned to receive the control knob 102 such that outer portion of the control knob 102 is accessible to a clinician. In embodiments, the inner housing portion 108 of the proximal body portion 18 of the stapler reload 16 defines a flat 112 (FIG. 9) and the outer portion of the control knob 102 projects outwardly of the flat 112 and is accessible to a clinician. The flat 112 allows the outer surface of the control knob 102 to remain within the outer diameter (FIG. 9) of the proximal body portion 18 such that the proximal body portion 18 of the stapler reload 16 can be received within a small diameter trocar assembly.

In embodiments, the control knob 102 includes at least one protrusion 116 that is received in a respective recess 118 formed in the inner housing portion 108 of the proximal body portion 18 of the stapler reload 16 to retain the control knob 102 in a rotatably fixed position. As described in further detail below, the control knob 102 is rotatable from a first position (FIG. 11) in which the knife bar assembly 54 is engaged with the drive assembly 56 to a second position (FIG. 13) in which the knife bar assembly 54 is disengaged from the drive assembly 56.

Figure 10:
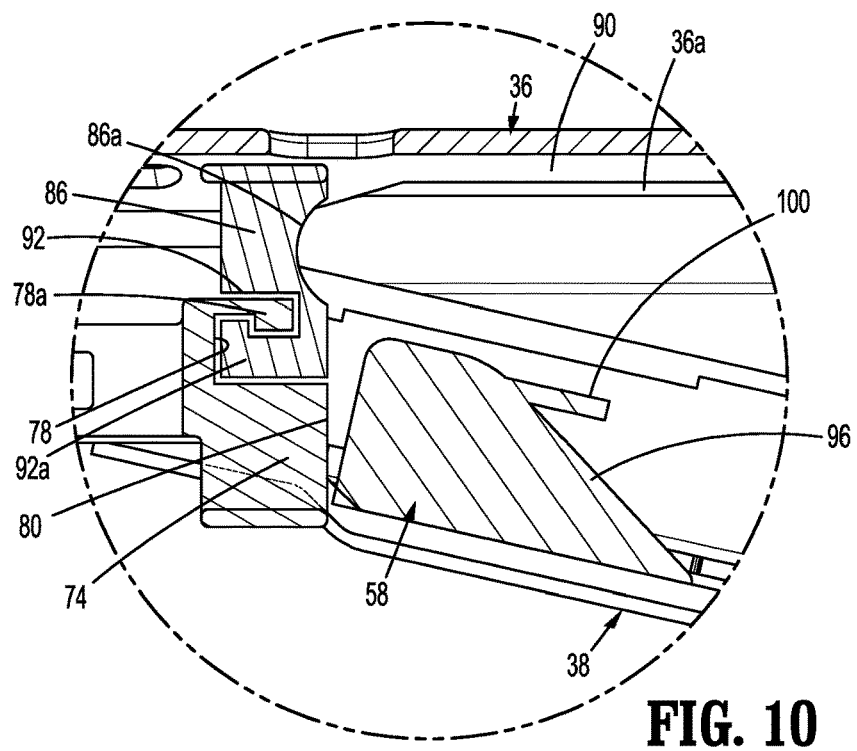
FIG. 10 is an enlarged view of the indicated area of detail shown in FIG. 8.
Figure 11:
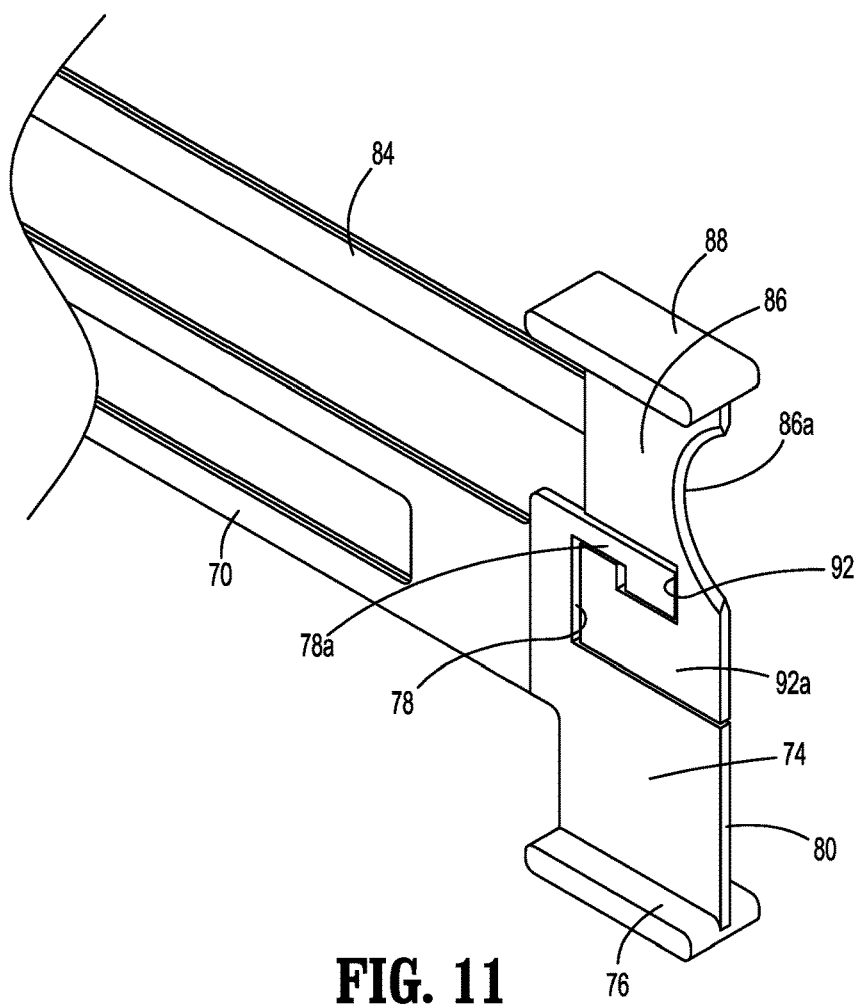
FIG. 11 is a side perspective view of a distal portion of a clamp and knife assembly of the tool assembly shown in FIG. 6 with a knife of the clamp and knife assembly engaged with the clamp of the clamp and knife assembly.

FIGS. 10 and 11 illustrate the control knob 102 in the first position with the knife bar assembly 54 engaged to the drive assembly 56. In the engaged position, the L-shaped leg 78a of the vertical strut 74 of the drive assembly 56 is received within the L-shaped slot 92 of the vertical strut 86 of the knife bar assembly 54 and the L-shaped leg 92a of the vertical strut 86 of the knife bar assembly 54 is received within the L-shaped slot 78 of the vertical strut 74 of the drive assembly 56. When the knife bar assembly 54 is engaged with the drive assembly 56, advancement of the drive assembly 56 through the tool assembly 20 via actuation of the handle assembly 12 (FIG. 1) causes advancement of the knife bar assembly 54 through the tool assembly 20. As described above, advancement of the drive assembly 56 through the tool assembly 20 also advanced the actuation sled 58 through the tool assembly 20 to eject staples 62 from the staple cartridge 44.

Figure 12:
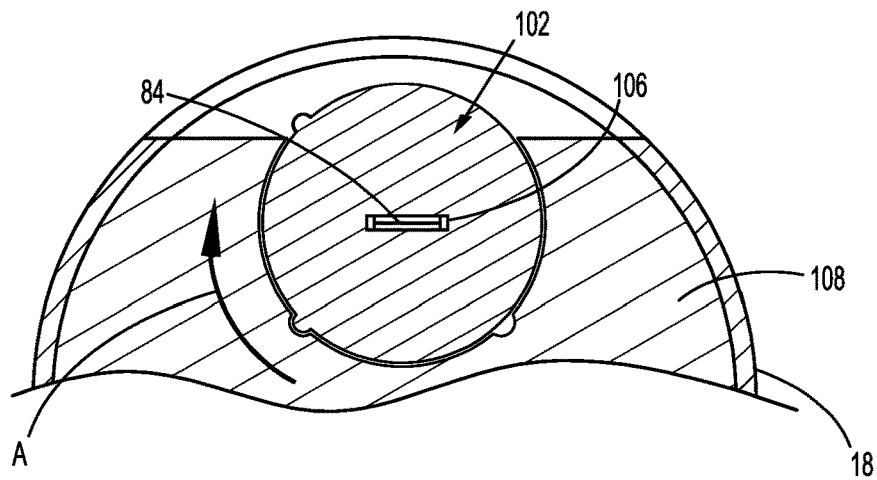
FIG. 12 is a cross-sectional view taken along section line 9-9 of FIG. 8 with as the knife assembly is moved to a position disengaged with the clamp of the clamp and knife assembly.
Figure 13:
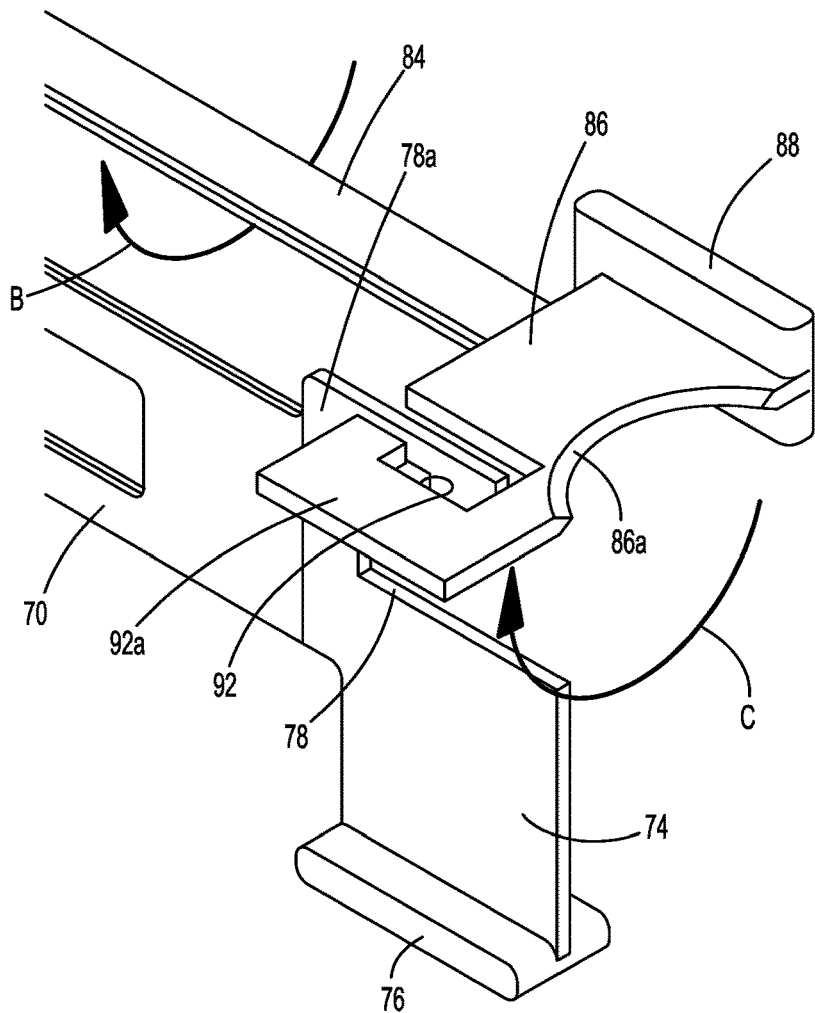
FIG. 13 is a side perspective view of the distal portion of the clamp and knife assembly of the tool assembly shown in FIG. 6 with the knife of the clamp and knife assembly disengaged from the clamp of the clamp and knife assembly.
Figure 18:
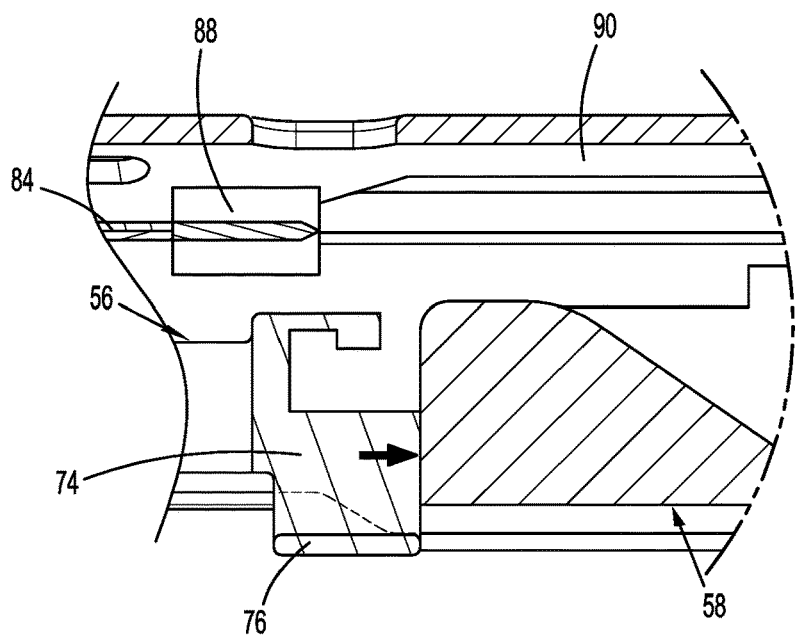
FIG. 18 is an enlarged view of the indicated area of detail shown in FIG. 17.
Figure 19:
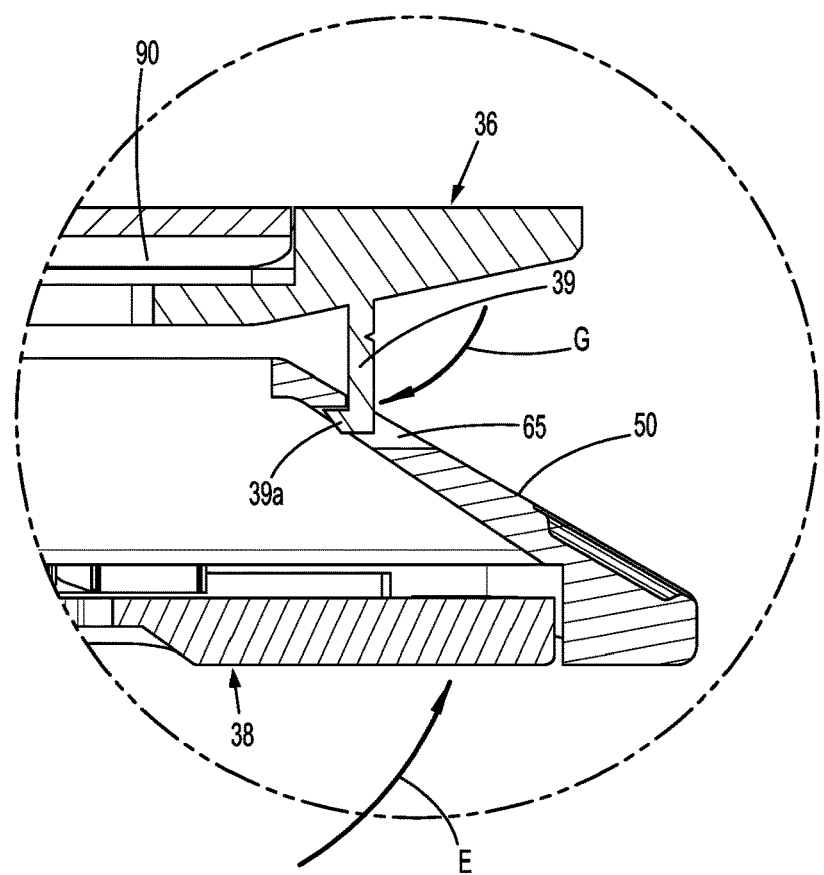
FIG. 19 is an enlarged view of the indicated area of detail shown in FIG. 17.

FIGS. 12 and 13 illustrate movement of the control knob 102 from the first position to the second position to move the knife bar assembly 54 and the drive assembly 56 from the engaged position (FIG. 11) to the disengaged position (FIG. 13). When the control knob 102 is rotated in the direction indicated by arrow "A" in FIG. 12, the drive member 84 of the knife bar assembly 54 is rotated about the rotation axis of the control knob 102 in the direction indicated by arrow "B" (FIG. 13) to cause rotation of the knife bar 82 about the rotation axis of the control knob 102 in the direction indicated by arrow "C" from engagement with the drive assembly 56. It is noted that the knife bar assembly 54 can only be rotated between the engaged and disengaged positions when the knife bar assembly 54 is in a fully retracted position with the vertical strut 86 of the knife bar 82 positioned proximally of the anvil channel 90 of the anvil 36 and of the knife slot 44a (FIG. 2) of the staple cartridge 44. Once the knife bar 82 is advanced to a position in which the knife bar 82 is engaged with the anvil 36 and the staple cartridge 44, rotation of the knife bar assembly 54 will be prevented.

FIGS. 14 and 15 illustrate the tool assembly 20 in the open position with the knife bar assembly 54 and the drive assembly 56 in a retracted position and the knife bar assembly 54 disengaged from the drive assembly 56. In this position, the lower beam 76 of the working member 72 of the drive assembly 56 is positioned proximally of the proximal end of the channel member 42 of the cartridge assembly 38. In this position, the knife bar 82 can be rotated via the control knob 102 in relation to the drive assembly 56 between the engaged position and the disengaged position.

FIGS. 16-19 illustrate the tool assembly 20 as the drive assembly 56 is advanced from the retracted position to an intermediate position in the direction indicated by arrows "D" to move the tool assembly 20 from the open position to the clamped position. As illustrated, the control knob 102 is in its second position and the knife bar assembly 54 is disengaged from the drive assembly 56. Movement of the drive assembly 56 in the direction of arrow "D" causes the lower beam 76 of the working member 72 to move into engagement with the angled cam surface 68a of the channel member 42 to pivot the cartridge assembly 38 in relation to the anvil 36 in the direction indicated by arrows "E" to the clamped position. As the distal portion of the staple cartridge 44 approaches the distal portion of the anvil 36, the locking member 39 of the anvil 36 engages the tissue guide portion 50 of the staple cartridge 44 and is deflected outwardly in the direction indicated by arrow "F" (FIG. 16) into the opening 65 of the staple cartridge 44. When the locking member 39 moves into the opening 65, the locking member 39 snaps back to its original configuration in the direction indicated by arrow "G" in FIG. 19 such that the hook portion 39a of the locking member 39 engages an inner wall of the staple cartridge 44 to secure the distal portions of the staple cartridge 44 and the anvil 36 in relation to each other.

The locking member 39 functions to define a maximum tissue gap between the staple cartridge 44 and the anvil 36 during firing of the tool assembly 20. It is noted that when the drive assembly 56 is advanced independently of the knife bar assembly 54, the upper beam 88 of the knife bar assembly 54 does not translate through the tool assembly 20 and, thus does not define the maximum tissue gap in the area of staple formation with the working member 72 of the drive assembly 56. The locking member 39 provides this function when the tool assembly 20 is fired without the knife bar 82.

FIGS. 20 and 21 illustrate the tool assembly 20 as the drive assembly 56 is advanced from the retracted position to the advanced position in the direction indicated by arrows "H" to eject staples 62 from the tool assembly 20. As the working member 72 of the drive assembly 56 is advanced through the tool assembly 20, the working member 72 engages and advances the actuation sled 58 through the tool assembly 20. As the actuation sled 58 approaches its advanced position, the finger 100 that extends from the distal end of the actuation sled 58 engages the flexible locking member 39 and forces the locking member 39 from the opening 65 to unlock the distal portions of the anvil 36 and cartridge assembly 38. This allows the tool assembly 20 to move partially towards the open position. In embodiments, the locking member 39 includes a notch 122 to facilitate bending of the locking member 39 upon contact with the finger 100.

Figure 22:
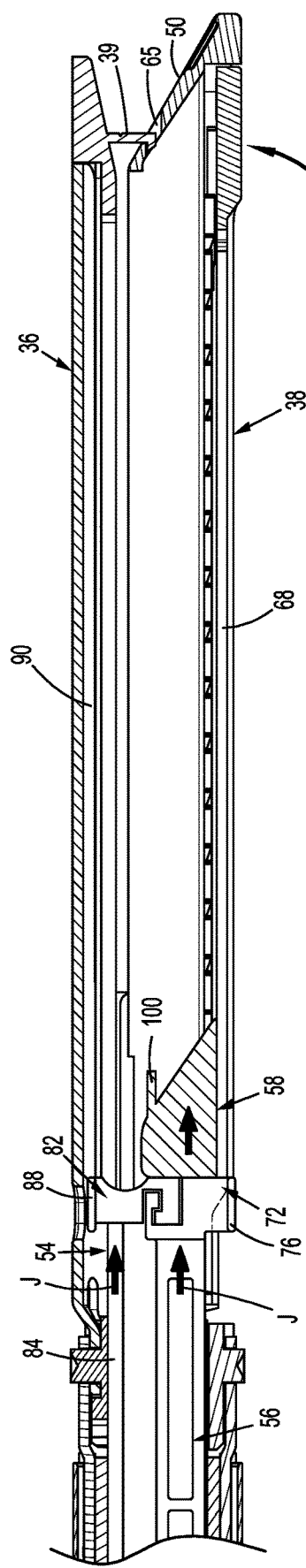
FIG. 22 is a cross-sectional view of the tool assembly of the surgical stapling device shown in FIG. 1 with the tool assembly in a clamped position as the clamp member begins to move from the retracted position towards the advanced position engaged with the knife assembly.
Figure 23:
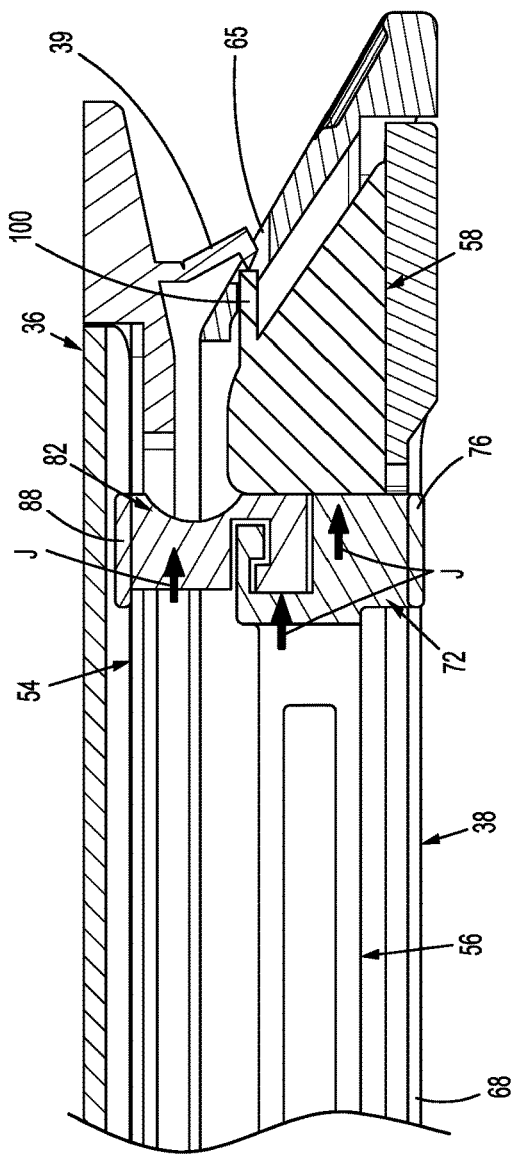
FIG. 23 is a cross-sectional view of the distal portion of the tool assembly of the stapling device shown in FIG. 1 with the clamp member in its advanced position engaged with the knife assembly and the tool assembly unlocked as the tool assembly moves towards the open position.

FIGS. 22 and 23 illustrate the drive assembly 56 as it is moved towards the advanced position engaged with the knife bar assembly 54. As discussed above, the knife bar assembly 54 can be rotated into engagement with the drive assembly 56 when the drive assembly 56 is in its fully retracted position by rotating the control knob 102 from its first position to its second position. When the drive assembly 56 is engaged with the knife bar assembly 54 and advanced in the direction indicated by arrows "J", the knife bar assembly 54 is advanced with the drive assembly 56 in the direction indicated by arrows "J". As the knife bar assembly 54 is advanced through the tool assembly 20, the upper beam 88 moves through the anvil channel 90 defined in the anvil 36. Since the knife bar 82 of the knife bar assembly 54 is engaged with the working member 72 of the drive assembly 56, the upper and lower beams 88 and 76 of the knife bar 82 and the working member 72, respectively, define a maximum tissue gap between the anvil 36 and the cartridge assembly 38. However, the locking member 39 is still received in the opening 65 of the staple cartridge 44 to provide additional stability to the tool assembly 20 during firing. The distally extending finger 100 of the actuation sled 58 functions as described above to release the locking member 39 from engagement with the staple cartridge 44 when the actuation sled 58 is advanced to its distal-most or advanced position.

The disclosed tool assembly 20 can be used in a cutting mode or a non-cutting mode by simply rotating the knife bar assembly 54 into and out of engagement with the drive assembly 56. The provision of the locking member 39 allows for a maximum tissue gap to be maintained between the anvil 36 and the cartridge assembly 38 when the stapling device 10 is actuated in the cutting mode or the non-cutting mode to improve the quality of staple formation. It is envisioned that the locking member 39, although shown on the anvil 36 could be incorporated onto the staple cartridge 44. It is also envisioned that the disclosed tool assembly 20 could be incorporated into a robotically controlled stapling device or include an electrically powered handle assembly.

Figure 24:
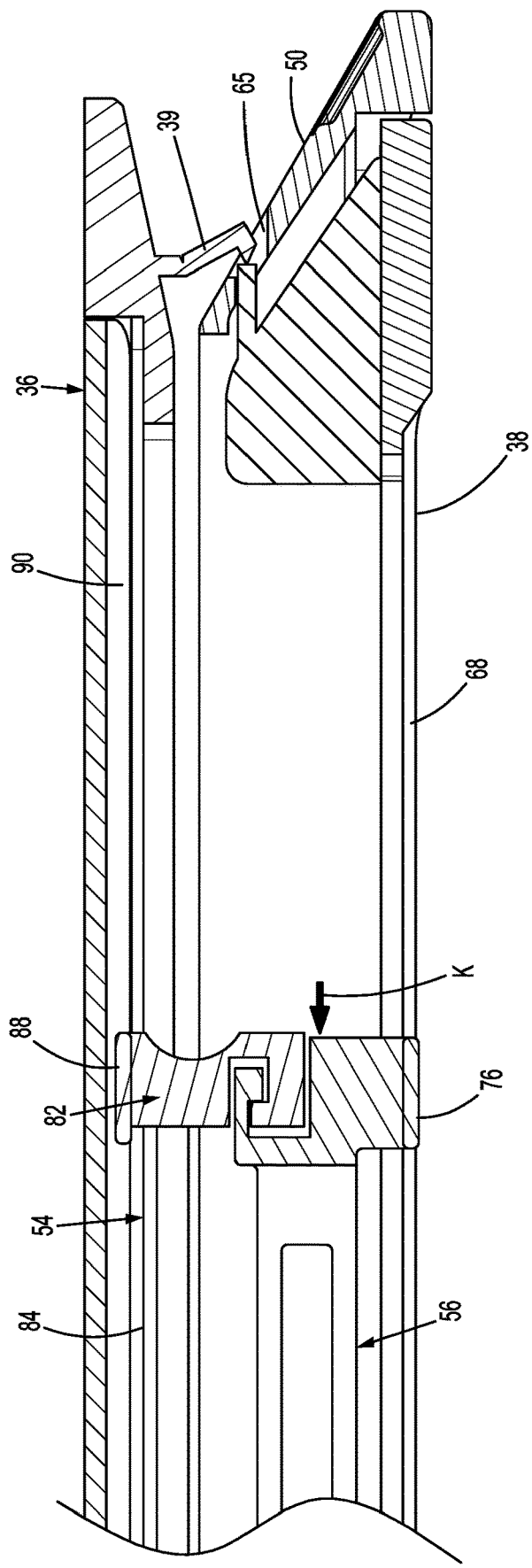
FIG. 24 is a cross-sectional view of the distal portion of the tool assembly of the stapling device shown in FIG. 1 as the clamp member and the knife assembly move the their retracted positions after the tool assembly has been fired.

FIG. 24 illustrates the drive assembly 56 as it is moved towards the retracted position engaged with the knife bar assembly 54. As the drive assembly 56 is retracted in the direction indicated by arrow "K", the knife bar assembly 54 is also retracted. When the drive assembly 56 and the knife bar assembly 54 are fully retracted, the tool assembly 20 can return to the open position (FIG. 1).

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A tool assembly comprising:
   an anvil defining an anvil channel and a knife slot communicating with the anvil channel;
   a cartridge assembly including a channel member and a staple cartridge, the channel member configured to receive the staple cartridge and defining a longitudinal slot, the staple cartridge supporting a plurality of staples and defining a knife slot that is aligned with the longitudinal slot;
   a drive assembly including a resilient beam and a working member, the working member including a first beam and a first vertical strut, the vertical strut including first engagement structure, the drive assembly movable in relation to the anvil and the cartridge assembly between advanced and retracted positions; and
   a knife bar assembly including a knife bar and a flexible drive member, the knife bar including a second beam and a second vertical strut, the second vertical strut supporting a knife and including second engagement structure, the knife bar assembly being selectively rotatable between first and second positions, wherein in the first position, the first and second engagement structures are coupled together such that movement of the drive assembly between the retracted and advanced positions causes corresponding movement of the knife bar assembly between the retracted and advanced positions, and in the second position, the first and second engagement structures are uncoupled such that the drive assembly is movable independently of the knife bar assembly between the retracted and advanced positions.

2. The tool assembly of claim 1, wherein one of the anvil and the cartridge assembly includes a locking member, the locking member being positioned on a distal portion of the one of the anvil and cartridge assembly and configured to engage the other of the anvil and cartridge assembly to secure the distal portions of the anvil and the cartridge assembly together and define a maximum tissue gap between the anvil and the cartridge assembly during firing of the tool assembly.

3. The tool assembly of claim 2, wherein the locking member includes a hook portion supported on the distal portion of the anvil and the staple cartridge defines an opening that receives the hook portion when the tool assembly is moved to a clamped position to secure the distal portion of the anvil to the distal portion of the cartridge assembly.

4. The tool assembly of claim 1, wherein the second beam is received with the anvil channel of the anvil and the second vertical strut extends through the knife slot of the anvil when the knife bar assembly is in the first position and is advanced within the tool assembly.

5. The tool assembly of claim 1, wherein the first engagement structure includes a first L-shaped slot and the second engagement structure includes a first L-shaped leg, the first L-shaped leg being received within the first L-shaped slot when the knife bar assembly is in the first position.

6. The tool assembly of claim 1, wherein the first engagement structure includes a first L-shaped slot and a first L-shaped leg and the second engagement structure includes a second L-shaped leg and a second L-shaped slot, the first L-shaped leg being received within the first L-shaped slot and the second L-shaped leg received within the second L-shaped slot when the knife bar assembly is in the first position.

7. A stapling device comprising:
an elongate body having a proximal portion and a distal portion; and
a tool assembly supported on the distal portion of the elongate body, the tool assembly including:
an anvil defining an anvil channel and a knife slot communicating with the anvil channel;
a cartridge assembly including a channel member and a staple cartridge, the channel member configured to receive the staple cartridge and defining a longitudinal slot, the staple cartridge supporting a plurality of staples and defining a knife slot that is aligned with the longitudinal slot;
a drive assembly including a resilient beam and a working member, the working member including a first beam and a first vertical strut, the first vertical strut including first engagement structure, the drive assembly movable in relation to the anvil and the cartridge assembly between advanced and retracted positions; and
a knife bar assembly including a knife bar and a flexible drive member, the knife bar including a second beam and a second vertical strut, the second vertical strut supporting a knife and including second engagement structure, the knife bar assembly being selectively rotatable between first and second positions, wherein in the first position, the first and second engagement structures are coupled together such that movement of the drive assembly between the retracted and advanced positions causes corresponding movement of the knife bar assembly between the retracted and advanced positions, and in the second position, the first and second engagement structures are uncoupled such that the drive assembly is movable independently of the knife bar assembly between the retracted and advanced positions.

8. The stapling device of claim 7, further including a control knob supported on the stapling device proximally of the tool assembly, the control knob secured to the flexible drive member of the knife bar assembly and rotatable to cause rotation of the knife bar assembly between the first position and the second position.

9. The stapling device of claim 8, wherein the control knob is supported on the elongate body at a location accessible to a clinician.

10. The stapling device of claim 9, wherein the elongate body includes an inner housing portion that defines a cylindrical cavity that receives the control knob, wherein the control knob does not extend outwardly of an outer diameter of the elongate body.

11. The stapling device of claim 10, wherein the control knob includes first and second protrusions and the inner housing portion of the elongate body includes at least one recess positioned to receive the first and second protrusions to retain the control knob in the first and second positions, respectively.

12. The stapling device of claim 7, wherein one of the anvil and the cartridge assembly includes a locking member, the locking member being positioned on a distal portion of the one of the anvil and cartridge assembly and configured to engage the other of the anvil and cartridge assembly to define a maximum tissue gap between the anvil and the cartridge assembly during firing of the tool assembly.

13. The stapling device of claim 12, wherein the locking member includes a hook portion supported on the distal portion of the anvil and the staple cartridge defines an opening that receives the hook portion when the tool assembly is moved to a clamped position to secure the distal portion of the anvil to the distal portion of the cartridge assembly.

14. The stapling device of claim 7, wherein the second beam is received with the anvil channel of the anvil and the second vertical strut extends through the knife slot of the anvil when the knife bar assembly is in the first position and is advanced within the tool assembly.

15. The stapling device of claim 7, wherein the first engagement structure includes a first L-shaped slot and the second engagement structure includes a first L-shaped leg, the first L-shaped leg being received within the first L-shaped slot when the knife bar assembly is in the first position.

16. The stapling device of claim 7, wherein the first engagement structure includes a first L-shaped slot and a first L-shaped leg and the second engagement structure includes a second L-shaped leg and a second L-shaped slot, the first L-shaped leg being received within the first L-shaped slot and the second L-shaped leg received within the second L-shaped slot when the knife bar assembly is in the first position.

* * * * *